United States Patent
Young et al.

[11] Patent Number: 5,932,582
[45] Date of Patent: Aug. 3, 1999

[54] FIBRINOGEN RECEPTOR ANTAGONIST PRODRUGS

[75] Inventors: Steven D. Young; George D. Hartman, both of Lansdale; Laura A. Libby, North Wales; Melissa S. Egbertson, Ambler; Donald E. Slaughter, Lansdale, all of Pa.

[73] Assignee: Merck & Co., Inc., Rahway, N.J.

[21] Appl. No.: 08/883,107

[22] Filed: Jun. 26, 1997

Related U.S. Application Data

[60] Provisional application No. 60/020,877, Jun. 28, 1996.

[51] Int. Cl.⁶ ........................ C07D 241/04; A61K 31/495
[52] U.S. Cl. ........................ 514/255; 544/392; 544/393; 544/395
[58] Field of Search ..................... 544/365, 360, 544/372, 382, 383, 384, 385, 386, 389, 392, 393, 395; 514/255

[56] References Cited

U.S. PATENT DOCUMENTS 5,648,368  7/1997  Egbertson et al. ...................... 514/331

FOREIGN PATENT DOCUMENTS

| 659 743 A1 | 6/1995 | European Pat. Off. . |
|---|---|---|
| 718 287 A2 | 12/1995 | European Pat. Off. . |
| 44 46 301 A1 | 12/1994 | Germany . |
| 2 276 163 | 3/1993 | United Kingdom . |
| 2276165 | 9/1994 | United Kingdom . |
| WO 94 22834 | 10/1994 | WIPO . |
| WO 96/16942 | 11/1994 | WIPO . |

*Primary Examiner*—Mukund J. Shah
*Assistant Examiner*—Deepak Rao
*Attorney, Agent, or Firm*—Richard S. Parr; Melvin Winokur

[57] ABSTRACT

Fibrinogen receptor antagonist alcohol prodrugs having the structure, for example, of

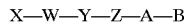

more particularly,

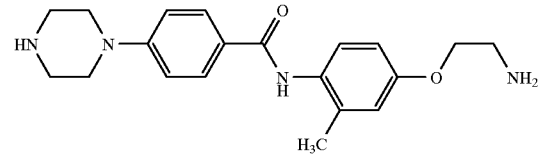

12 Claims, No Drawings

FIBRINOGEN RECEPTOR ANTAGONIST PRODRUGS

This application claims the benefit of U.S. Provisional Application No. 60/020,877, filed Jun. 28, 1996.

BACKGROUND OF THE INVENTION

The invention relates generally to modulating cell adhesion and to inhibiting the binding of fibrinogen and other proteins to blood platelets, and inhibiting the aggregation of blood platelets specifically to the gp IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothelial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in *Science*, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in *Proc. Nat'l Acad. Sci. U.S.A.*, 84, 6471–6475, (1987), describes an Arg-Gly-Asp directed adhesion receptor expressed by human endothelial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. of Biol. Chem.*, 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the stereochemical conformation of Arg-Oly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In *Proc. Nat'l Acad. Sci. U.S.A.*, 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661, 111 and U.S. Pat. No. 4,578,079.

Ruggeri et al., *Proc. Nat'l Acad. Sci. U.S.A.*, 83, 5708–5712 (1986) explore a series of synthetic peptides designed in lengths to 16 residues, that contain ROD and a valine attached to the aspartic acid residue of RGD that inhibit fibrinogen binding to platelets. See also Koczewiak et al., *Biochem.* 23, 1767–1774 (1984); Ginsberg et al., *J. Biol. Chem.* 260(7), 3931–3936 (1985); and Haverstick et al., *Blood* 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa a complex. For example, Huang et al., *J. Biol Chem.*, 262, 16157–16163 (1987); Huang et al., *Biochemistry*, 28, 661–666 (1989) describe the primary structure of the venom trigramin which is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., *J. Biol. Chem.*, 263, 19827–19832 (1988). See also, Dennis et al., *Proc. Nat'l Acad. Sci. USA*, 87, 2471–2475 (1989). However, these snake venom factors also have high affinity for other members of the adhesive protein receptor family including the vitronectin and fibronectin receptors so are not selective for the gp IIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No. 5,023,233 discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IIIa receptor. U.S. Pat. No. 5,037,808 discloses guanidino peptide mimetic compounds that retain an Asp residue which inhibit platelet aggregation. WO9014103 describes the use of antibody-poly-peptide conjugates wherein said polypeptides contain the Arg-Gly-Asp (RGD) sequence.

WO9111458 discloses the use of large cyclic peptides containing RGD flanked by proline residues which are platelet aggregation inhibitors. WO9101331 discloses small cyclic platelet aggregation inhibitors which are synthetic cyclic pentapeptides containing the tripeptide sequence Arg-Gly-Asp and a thioether linkage in the cycle. U.S. Pat. No. 5,051,405 also discloses the use of peptides and pseudopeptides such as N-amidino-piperidine-3-carboxylglycyl-L-aspartyl-L-valine that inhibit platelet aggregation and thrombus formation in mammalian blood. EP 445 796 discloses linear compounds which can include internal piperazinyl or piperidinyl derivatives. EP437 367 discloses linear polypeptide fibrinogen receptor antagonists. U.S. Pat. No. 5,256,/812 discloses compounds of the $R^1$—A—(W)$_a$—X—$(CH_2)_b$—$(Y)_c$—B—Z—COOR wherein $R^1$ is a guandidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonist pro-drugs of antagonists that have significant binding activity and are, therefore, useful for the reasons stated herein.

SUMMARY OF THE INVENTION

The invention relates to compounds having the formula

X—W—Y—Z—(A)$_r$—B and pharmaceutically acceptable salts, wherein
W is —(CH$_2$)$_q$—, wherein q is 0 or 2;
X is
  a 5, 6 or 7 membered aromatic or nonaromatic ring, having 1, 2 or 3 heteroatoms selected from N, O, and S, and either unsubstituted or monosubstituted on carbon and nitrogen atoms with R$^1$, or disubstituted on carbon and nitrogen atoms with R$^1$ and R$^2$, where R$^1$ and R$^2$ are independently selected from the group consisting of
  hydrogen,
  halogen,
  C$_{1-10}$ alkyl,
  C$_{3-8}$ cycloalkyl,
  aryl,
  aryl C$_{1-8}$ alkyl,
  amino,
  amino C$_{1-8}$ alkyl,
  C$_{1-3}$ acylamiino,
  C$_{1-3}$ acylamino C$_{1-8}$ alkyl,
  C$_{1-6}$ alkylamino,
  C$_{1-6}$ alkylamino C$_{1-8}$ alkyl,
  C$_{1-6}$ dialkylamino,
  C$_{1-6}$ dialkylamino C$_{1-8}$ alkyl,
  C$_{1-6}$ alkoxy,
  C$_{1-6}$ alkoxy C$_{1-6}$ alkyl,
  aryl C$_{1-6}$ alkyloxy,
  aryl C$_{1-6}$ alkyloxy C$_{1-6}$ alkyl,
  carboxy C$_{1-6}$ alkyl,
  C$_{1-3}$ alkoxycarbonyl,
  C$_{1-3}$ alkoxycarbonyl C$_{1-6}$ alkyl,
  carboxy,
  carboxy C$_{1-6}$ alkyloxy,
  hydroxy, and
  hydroxy C$_{1-6}$ alkyl, or
  a 9 or 10 membered fused aromatic or nonaromatic ring, having 1, 2 or 3 heteroatoms selected from N, O, and S, and either unsubstituted or monosubstituted on carbon and nitrogen atoms with R$^1$, or disubstituted on carbon and nitrogen atoms with R$^1$ and R$^2$, where R$^1$ and R$^2$ are independently selected from the group consisting of
  hydrogen,
  halogen,
  C$_{1-10}$ alkyl,
  C$_{3-8}$ cycloalkyl,
  aryl,
  aryl C$_{1-8}$ alkyl,
  amino,
  amino C$_{1-8}$ alkyl,
  C$_{1-3}$ acylamino,
  C$_{1-3}$ acylamino C$_{1-8}$ alkyl,
  C$_{1-6}$ alkylamino,
  C$_{1-6}$ alkylamino C$_{1-8}$ alkyl,
  C$_{1-6}$ diallkylamino,
  C$_{1-6}$ dialkylamino C$_{1-8}$ alkyl,
  C$_{1-6}$ alkoxy,
  C$_{1-6}$ alkoxy C$_{1-6}$ alkyl,
  aryl C$_{1-6}$ alkyloxy,
  aryl C$_{1-6}$ alkyloxy C$_{1-6}$ alkyl,
  carboxy C$_{1-6}$ alkyl,
  C$_{1-3}$ alkoxycarbonyl,
  C$_{1-3}$ alkoxycarbonyl C$_{1-6}$ alkyl,
  carboxy,
  carboxy C$_{1-6}$ alkyloxy,
  hydroxy, and
  hydroxy C$_{1-6}$ alkyl,
Y is
  a 5 or 6 membered aromatic or non-aromatic ring, having 0, 1, 2 or 3 heteroatoms selected from N, O, and S, and either unsubstituted or substituted on carbon or nitrogen atoms with R$^3$ selected from the group consisting of
  hydrogen,
  halogen,
  C$_{1-10}$ alkyl,
  C$_{3-8}$ cycloalkyl,
  aryl,
  aryl C$_{1-8}$ alkyl,
  amino,
  amino C$_{1-8}$ alkyl,
  C$_{1-3}$ acylamino,
  C$_{1-3}$ acylamino C$_{1-8}$ alkyl,
  C$_{1-6}$ alkylamino,
  C$_{1-6}$ alkylamino C$_{1-8}$ alkyl,
  C$_{1-6}$ dialkylamino,
  C$_{1-6}$ dialkylamino C$_{1-8}$ alkyl,
  C$_{1-6}$ alkoxy,
  C$_{1-6}$ alkoxy C$_{1-6}$ alkyl,
  aryl C$_{1-6}$ alkyloxy,
  aryl C$_{1-6}$ alkyloxy C$_{1-6}$ alkyl,
  carboxy C$_{1-6}$ alkyl,
  C$_{1-3}$ alkoxycarbonyl,
  C$_{1-3}$ alkoxycarbonyl C$_{1-6}$ alkyl,
  carboxy,
  carboxy C$_{1-6}$ alkyloxy,
  hydroxy,
  hydroxy C$_{1-6}$ alkyl,
  or
Y is a δ-lactam,
  or
Y is or
X and Y, provided that q=0, together form , or

;

Z is

—(CH$_2$)$_m$—C(=O)—N(R$^4$)—(CH$_2$)$_n$—,

—(CH$_2$)$_m$—N(R$^4$)—C(=O)—(CH$_2$)$_n$—,

—CH$_2$CH$_2$—,

—CH=CH—,

—CH$_2$—O—,

—O—CH$_2$—,

—C(=O)—CH$_2$—,

—CH$_2$—C(=O)—,

—CH$_2$NR$^4$—,

—NR$^4$CH$_2$—,

—SO$_2$—NR$^4$—,

—NR$^4$—SO$_2$—,

—CH(OH)—CH$_2$—, or

—CH$_2$—CH(OH)—;

R$^4$ is selected from the group consisting of
  hydrogen,
  halogen,
  C$_{1-10}$ alkyl,
  C$_{3-8}$ cycloalkyl,
  aryl,
  aryl C$_{1-8}$ alkyl,
  amino,
  amino C$_{1-8}$ alkyl,
  C$_{1-3}$ acylamino,
  C$_{1-3}$ acylamino C$_{1-8}$ alkyl,
  C$_{1-6}$ alkylamino,
  C$_{1-6}$ alkylamino C$_{1-8}$ alkyl,
  C$_{1-6}$ dialkylamino,
  C$_{1-6}$ dialkylamino C$_{1-8}$ alkyl,
  C$_{1-4}$ alkoxy,
  C$_{1-4}$ alkoxy C$_{1-6}$ alkyl,
  carboxy,
  carboxy $_{1-6}$ alkyl,
  C$_{1-3}$ alkoxycarbonyl,
  C$_{1-3}$ alkoxycarbonyl C$_{1-6}$ alkyl,
  carboxy C$_{1-6}$ alkyloxy,
  hydroxy, and
  hydroxy C$_{1-6}$ alkyl;

A is
  a 5 or 6 membered aromatic ring, having 0, 1, 2 or 3 heteroatoms
    selected from N, O, and S, and either unsubstituted or monosubstituted on carbon or nitrogen atoms with R$^5$, or disubstituted on carbon or nitrogen atoms with R$^5$ and R$^6$, or trisubstituted on carbon or nitrogen atoms with R$^5$, R$^6$ and R$^{10}$, where R$^5$, R$^6$ and R$^{10}$ are independently selected from the group consisting of
    hydrogen,
    halogen,
    C$_{3-8}$ cycloalkyl,
    aryl,
    aryl C$_{1-8}$ alkyl,
    amino,
    amino C$_{1-8}$ alkyl,
    C$_{1-3}$ acylamino,
    C$_{1-3}$ acylamino C$_{1-8}$ alkyl,
    C$_{1-6}$ alkylamino,
    C$_{1-6}$ alkylamino C$_{1-8}$ alkyl,
    C$_{1-6}$ dialkylamino,
    C$_{1-6}$ dialkylamino C$_{1-8}$ alkyl,
    C$_{1-6}$ alkoxy,
    C$_{1-6}$ alkoxy C$_{1-6}$ alkyl,
    aryl C$_{1-6}$ alkyloxy,
    aryl C$_{1-6}$ alkyloxy C$_{1-6}$ alkyl,
    carboxy C$_{1-6}$ alkyl,
    C$_{1-3}$ alkoxycarbonyl,
    C$_{1-3}$ alkoxycarbonyl C$_{1-6}$ alkyl,
    carboxy,
    carboxy C$_{1-6}$ alkyloxy,
    hydroxy, and
    hydroxy C$_{1-6}$ alkyl, or
  a 9 or 10 membered fused aromatic ring, having 0, 1, 2 or 3 heteroatoms selected from N, O, and S, and either unsubstituted or monosubstituted on carbon or nitrogen atoms with R$^5$, or disubstituted on carbon or nitrogen atoms with R$^5$ and R$^6$, or trisubstituted on carbon or nitrogen atoms with R$^5$, R$^6$ and R$^{10}$, where R$^5$, R$^6$ and R$^{10}$ are independently selected from the group consisting of
    hydrogen,
    halogen,
    C$_{1-10}$ alkyl,
    C$_{3-8}$ cycloalkyl,
    aryl,
    aryl C$_{1-8}$ alkyl,
    amino,
    amino C$_{1-8}$ alkyl,
    C$_{1-3}$ acylamino,
    C$_{1-3}$ acylamino C$_{1-8}$ alkyl,
    C$_{1-6}$ alkylamino,
    C$_{1-6}$ alkylamino C$_{1-8}$ alkyl,
    C$_{1-6}$ dialkylamino,
    C$_{1-6}$ dialkylamino C$_{1-8}$ alkyl,
    C$_{1-6}$ alkoxy,
    C$_{1-6}$ alkoxy C$_{1-6}$ alkyl,
    aryl C$_{1-6}$ alkyloxy, aryl $C_{1-6}$ alkyloxy $C_{1-6}$ alkyl,
carboxy $C_{1-6}$ alkyl,
$C_{1-3}$ alkoxycarbonyl,
$C_{1-3}$ alkoxycarbonyl $C_{1-6}$ alkyl,
carboxy,
carboxy $C_{1-6}$ alkyloxy,
hydroxy,
hydroxy $C_{1-6}$ alkyl, or
—CH$_2$C(O)NH(CH$_2$)$_s$—;
r is 0 or 1;
B is —O(CH$_2$)$_p$CH$_2$N(R$^8$R$^7$),
—CH$_2$(CH$_2$)$_t$CH$_2$N(R$^8$R$^7$),
—CH(CH$_2$)$_t$CH$_2$N(R$^8$R$^7$), or
  |
  R$^9$

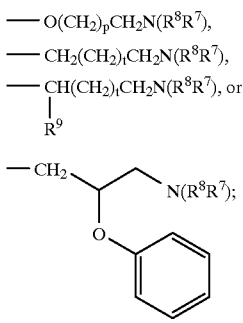

$R^7$, $R^8$, and $R^9$ are independently selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy,
carboxy $C_{1-6}$ alkyloxy,
hydroxy, and
hydroxy $C_{1-6}$ alkyl;
m is 0, 1, 2, 3, or 4;
n is an integer from 0 to 6;
p is 1, 2, 3 or 4;
s is an integer from 0 to 6; and
t is 0, 1, 2, 3 or 4.

The compounds are useful as prodrugs of fibrinogen receptor antagonists.

The invention also includes the use of a compound of the invention, or a pharmaceutically acceptable salt thereof, in the manufacture of a medicament for inhibiting the aggregation of blood platelets, preventing platelet thrombosis, preventing thromboembolism or preventing reocclusion, in a mammal.

DETAILED DESCRIPTION OF THE INVENTION

The invention relates to compounds having the formula

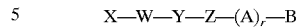

and pharmaceutically acceptable salts, wherein
W is —(CH$_2$)$_q$—, wherein q is 0 or 2;
X is
  a 5, 6 or 7 membered aromatic or nonaromatic ring, having 1, 2 or 3 heteroatoms selected from N, O, and S, and either unsubstituted or monosubstituted on carbon and nitrogen atoms with $R^1$, or disubstituted on carbon and nitrogen atoms with $R^1$ and $R^2$, where $R^1$ and $R^2$ are independently selected from the group consisting of
  hydrogen,
  halogen,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-6}$ alkoxy,
  $C_{1-6}$ alkoxy $C_{1-6}$ alkyl,
  aryl $C_{1-6}$ alkyloxy,
  aryl $C_{1-6}$ alkyloxy $C_{1-6}$ alkyl,
  carboxy $C_{1-6}$ alkyl,
  $C_{1-3}$ alkoxycarbonyl,
  $C_{1-3}$ alkoxycarbonyl $C_{1-6}$ alkyl,
  carboxy,
  carboxy $C_{1-6}$ alkyloxy,
  hydroxy, and
  hydroxy $C_{1-6}$ alkyl, or
a 9 or 10 membered fused aromatic or nonaromatic ring, having 1, 2 or 3 heteroatoms selected from N, O, and S, and either unsubstituted or monosubstituted on carbon and nitrogen atoms with $R^1$, or disubstituted on carbon and nitrogen atoms with $R^1$ and $R^2$, where $R^1$ and $R^2$ are independently selected from the group consisting of
  hydrogen,
  halogen,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-6}$ alkoxy,
  $C_{1-6}$ alkoxy $C_{1-6}$ alkyl,
  aryl $C_{1-6}$ alkyloxy,
  aryl $C_{1-6}$ alkyloxy $C_{1-6}$ alkyl,
  carboxy $C_{1-6}$ alkyl, $C_{1-63}$ alkoxycarbonyl,
$C_{1-3}$ alkoxycarbonyl $C_{1-6}$ alkyl,
carboxy,
carboxy $C_{1-6}$ alkyloxy,
hydroxy, and
hydroxy $C_{1-6}$ alkyl, Y is
a 5 or 6 membered aromatic or non-aromatic ring, having 0, 1, 2 or 3 heteroatoms selected from N, O, and S, and either unsubstituted or substituted on carbon or nitrogen atoms with $R^3$ selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy $C_{1-6}$ alkyl,
$C_{1-3}$ alkoxycarbonyl,
$C_{1-3}$ alkoxycarbonyl $C_{1-6}$ alkyl,
carboxy,
carboxy $C_{1-6}$ alkyloxy,
hydroxy,
hydroxy $C_{1-6}$ alkyl, or Y is a δ-lactam, or Y is

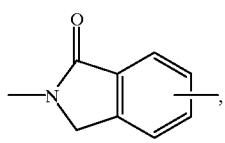

or

X and Y, provided that q=0, together form

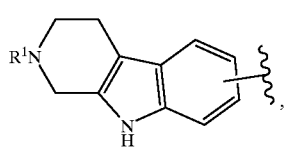

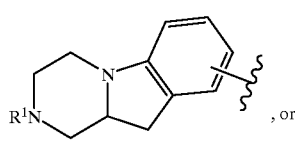, or

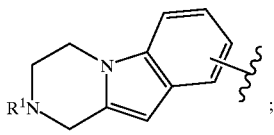;

Z is

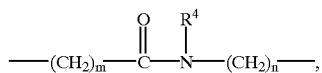

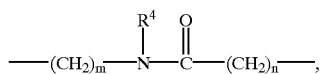

—CH$_2$CH$_2$—,

—CH=CH—,

—CH$_2$—O—,

—O—CH$_2$—,

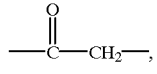

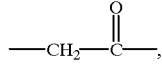

—CH$_2$NR$^4$—,

—NR$^4$CH$_2$—,

—SO$_2$—NR$^4$—,

—NR$^4$—SO$_2$—,

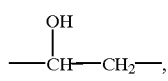

or

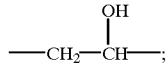;

$R^4$ is selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-4}$ alkoxy,
$C_{1-4}$ alkoxy $C_{1-6}$ alkyl,
carboxy,
carboxy $_{1-6}$ alkyl,
$C_{1-3}$ alkoxycarbonyl,
$C_{1-3}$ alkoxycarbonyl $C_{1-6}$ alkyl, carboxy $C_{1-6}$ alkyloxy,
hydroxy, and
hydroxy $C_{1-6}$ alkyl;

A is
a 5 or 6 membered aromatic ring, having 0, 1, 2 or 3 heteroatoms
selected from N, O, and S, and either unsubstituted or monosubstituted on carbon or nitrogen atoms with $R^5$, or disubstituted on carbon or nitrogen atoms with $R^5$ and $R^6$, or trisubstituted on carbon or nitrogen atoms with $R^5$, $R^6$ and $R^{10}$, where $R^5$, $R^6$ and $R^{10}$ are independently selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy $C_{1-6}$ alkyl,
$C_{1-3}$ alkoxycarbonyl,
$C_{1-3}$ alkoxycarbonyl $C_{1-6}$ alkyl,
carboxy,
carboxy $C_{1-6}$ alkyloxy,
hydroxy, and
hydroxy $C_{1-6}$ alkyl, or
a 9 or 10 membered fused aromatic ring, having 0, 1, 2 or 3 heteroatoms selected from N, O, and S, and either unsubstituted or monosubstituted on carbon or nitrogen atoms with $R^5$, or disubstituted on carbon or nitrogen atoms with $R^5$ and $R^6$, or trisubstituted on carbon or nitrogen atoms with $R^5$, $R^6$ and $R^{10}$, where $R^5$, $R^6$ and $R^{10}$ are independently selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy $C_{1-6}$ alkyl,
$C_{1-3}$ alkoxycarbonyl,
$C_{1-3}$ alkoxycarbonyl $C_{1-6}$ alkyl,
carboxy,
carboxy $C_{1-6}$ alkyloxy,
hydroxy,
hydroxy $C_{1-6}$ alkyl, or
—$CH_2C(O)NH(CH_2)_s$—;

r is 0 or 1;

B is

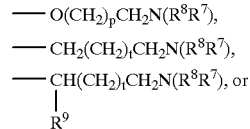
—$O(CH_2)_pCH_2N(R^8R^7)$,
—$CH_2(CH_2)_tCH_2N(R^8R^7)$,
—$CH(CH_2)_tCH_2N(R^8R^7)$, or
  |
  $R^9$

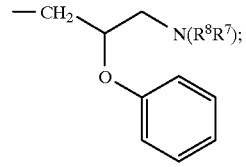

$R^7$, $R^8$, and $R^9$ are independently selected from the group consisting of
hydrogen,
halogen,
$C_{1-10}$ alkyl,
$C_{3-8}$ cycloalkyl,
aryl,
aryl $C_{1-8}$ alkyl,
amino,
amino $C_{1-8}$ alkyl,
$C_{1-3}$ acylamino,
$C_{1-3}$ acylamino $C_{1-8}$ alkyl,
$C_{1-6}$ alkylamino,
$C_{1-6}$ alkylamino $C_{1-8}$ alkyl,
$C_{1-6}$ dialkylamino,
$C_{1-6}$ dialkylamino $C_{1-8}$ alkyl,
$C_{1-6}$ alkoxy,
$C_{1-6}$ alkoxy $C_{1-6}$ alkyl,
aryl $C_{1-6}$ alkyloxy,
aryl $C_{1-6}$ alkyloxy $C_{1-6}$ alkyl,
carboxy,
carboxy $C_{1-6}$ alkyl,
$C_{1-3}$ alkoxycarbonyl,
$C_{1-3}$ alkoxycarbonyl $C_{1-6}$ alkyl,
carboxy,
carboxy $C_{1-6}$ alkyloxy,
hydroxy, and
hydroxy $C_{1-6}$ alkyl;
m is 0, 1, 2, 3, or 4;
n is an integer from 0 to 6;
p is 1, 2, 3 or 4;
s is an integer from 0 to 6; and
t is 0, 1, 2, 3 or 4.

In one class of compounds, the compound has the formula

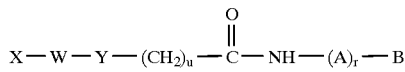

$$X-W-Y-(CH_2)_u-\overset{O}{\underset{\|}{C}}-NH-(A)_r-B$$

and pharmaceutically acceptable salts, wherein
u is 0, 1, or 2;
W is —$(CH_2)_q$—, wherein q is 0 or 2;
X is a 6-membered aromatic or nonaromatic ring having 1, 2 or 3 nitrogen atoms, unsubstituted or substituted on carbon or nitrogen atoms with $NH_2$, Y is a 6-membered aromatic or nonaromatic ring having 0, 1, 2 or 3 nitrogen atoms,
or
Y is a δ-lactam,
or
Y is

[structure: N-methyl isoindolinone]

or
X and Y, provided that q=0, together form

[structure: tetrahydro-β-carboline with HN and NH]

;

A is
is a 6-membered aromatic ring unsubstituted, mono substituted with a moiety selected from the group consisting of halogen, $C_{1-3}$ alkyl, or $C_{1-3}$ alkylsulfonyl amino, disubstituted with one or more moieties, same or different, selected from the group consisting of halogen, $C_{1-3}$ alkyl, or $C_{1-3}$ alkylsulfonyl amino, or trisubstituted with one or more moieties, same or different, selected from the group consisting of halogen, $C_{1-3}$ alkyl, or $C_{1-3}$ alkylsulfonyl amino;
r is 0 or 1;
B is —O(CH$_2$)$_2$NH$_2$, —CH$_2$C(OPh)HCH)$_2$NH$_2$, —CH(CH$_3$)(CH$_2$)$_2$NH$_2$,
and all other substituents are as previously defined.
In a subclass of the class, the compounds have the formula $$X-W-Y-(CH_2)_u-\overset{O}{\underset{\|}{C}}-NH-(A)_r-B$$

and pharmaceutically acceptable salts, wherein
u is 0, 1, or 2;
W is —(CH$_2$)$_q$—, wherein q is 0 or 2;
X is a 6-membered aromatic or nonaromatic ring having 1 or 2 nitrogen atoms, unsubstituted or substituted on carbon or nitrogen atoms with NH$_2$,
Y is a 6-membered aromatic or nonaromatic ring having 0 or 1 nitrogen atoms, or
a δ-lactam,
or X and Y, provided that q=0, together form

[structure: tetrahydro-β-carboline]

;

A is
a 6-membered aromatic ring unsubstituted, mono substituted with Br, CH$_3$, or NHSO$_2$CH$_3$, disubstituted with one or more moieties, same or different, selected from the group consisting of Br, CH$_3$, and NHSO$_2$CH$_3$, or trisubstituted with one or more moieties, same or different, selected from the group consisting of Br, CH$_3$, and NHSO$_2$CH$_3$; and
r is 0 or 1;
B is —O(CH$_2$)$_2$NH$_2$, —CH$_2$C(OPh)HCH$_2$NH$_2$, —CH(CH$_3$)(CH$_2$)$_2$NH$_2$, and all other substituents are as previously defined.

In a group of this subclass, the compounds have the formula $$X-W-Y-(CH_2)_u-\overset{O}{\underset{\|}{C}}-NH-(A)_r-B$$

and pharmaceutically acceptable salts, wherein u is 0 or 1;
X is

[structure: piperazinyl with HN]

,

[structure: 2-aminopyridin-4-yl]

,

[structure: 2-aminopyridin-3-yl with NH$_2$]

, or

[structure: piperidin-4-yl with HN]

;

W is —(CH$_2$)$_q$—, wherein q is 0 or 2;
Y is

[structure: 1,4-phenylene]

,

[structure: 2-oxo-piperidinyl]

, or

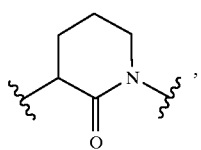,
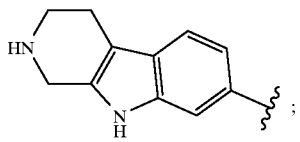
or X and Y, provided that q=0, together form
A is
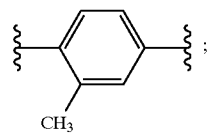;
r is 0 or 1;
B is —O(CH$_2$)$_2$NH$_2$, —CH$_2$C(OPh)HCH$_2$NH$_2$, —CH(CH$_3$)(CH$_2$)$_2$NH$_2$,
and all other substituents are as previously defined.
Specific exemplifications of this group are shown below:
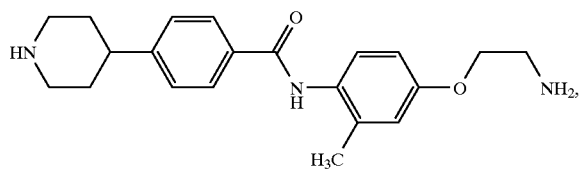
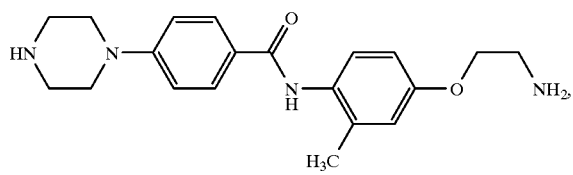
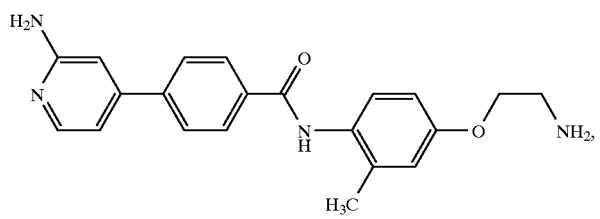
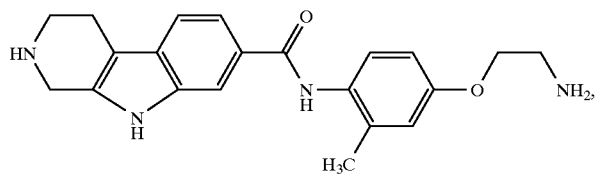
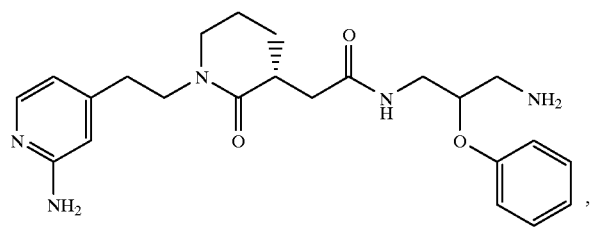,
and -continued

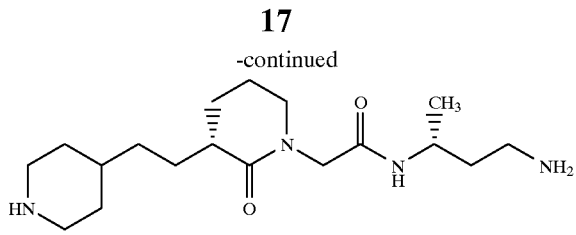

and pharmaceutically acceptable salts.

The active acids of these compounds have been evaluated in vitro and found to have an $IC_{50}$ for inhibiting platelet aggregation of between about 8 nM and 10 μM.

The prodrugs may be administered in low amounts relative to the amounts of antagonist that would ordinarily be administered. The prodrugs may be administered orally. The prodrugs retain structural integrity while passing though the gastrointestinal system, and are effectively delivered to cells. They are subjected to metabolic reactions to form the active acid which then interacts with the platelet receptor site.

A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

One test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the acids of the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2 \times 10^8$ per ml), fibrinogen (100 micrograms per ml (ug/ml)), $Ca^{2+}$ (1 mM), and the compound to be tested. The aggregation is initiated by adding 10 m ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

Additionally, these compounds are useful for treating mammals suffering from a bone condition caused or mediated by increased bone resorption, who are in need of such therapy. Pharmacologically effective amounts of the compounds, including pharmaceutically acceptable salts thereof, are administered to the mammal, to inhibit the activity of mammalian osteoclasts.

Additionally, these compounds are useful for treating angiogenesis (formation of new blood vessels). It has been postulated that the growth of tumors depends on an adequate blood supply, which in turn is dependent on the growth of new vessels into the tumor. Inhibition of angiogenesis can cause tumor regression in animal models. (See, *Harrison's Principles of Internal Medicine*, 12th ed., 1991). These compounds are therefore useful in the treatment of cancer for inhibiting tumor growth. (See e.g., Brooks et al., *Cell*, 79:1157–1164 (1994)).

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teociate, tosylate, triethiodide, valerate.

Compounds of the present invention may be chiral; included within the scope of the present invention are racemic mixtures and separated enantiomers of the general formula. Furthermore, all diastereomers, including E, Z isomers, of the general formula are included in the present scope. Furthermore, hydrates as well as anhydrous compositions and polymorphs of the general formula are within the present invention.

The compounds of the invention are prodrugs of active acids which inhibit fibrinogen binding to the gpIIb/IIIa platelet receptor site. These acids form in vivo, subsequent to administration to the patient, according to successive metabolic reactions, for example:

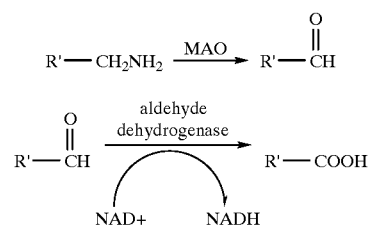

Compounds of the invention of the general formula R'—$CH_2NH_2$, may form aldehydes that metabolize into the active acid.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like, straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like, or straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "aryl" means a 5- or 6-membered aromatic ring containing 0, 1, or 2 heteroatoms selected from O, N, and S, e.g. phenyl, pyridine, pyrimidine, imidazole, thiophene, oxazole, isoxazole, thiazole, and amino- and halogen- substituted derivatives thereof.

The terms "alkyloxy" or "alkoxy" include an alkyl portion where alkyl is as defined above, e.g., methyloxy, propyloxy, and butyloxy.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit. Examples of arylalkyl include benzyL, fluorobenzyl, chlorobenzyl, phenylethyl, phenylpropyl, fluorophenylethyl, chlorophenylethyl, thienylmethyl, thienylethyl, and thienylpropyl. Examples of alkylaryl include toluene, ethylbenzene, propylbenzene, methylpyridine, ethylpyridine, propylpyridine, butylpyridine, butenylpyridine, and pentenylpyridine.

The term "halogen" includes fluorine, chlorine, iodine and bromine.

The term "oxy" means an oxygen (O) atom. The term "thio" means a sulfur (S) atom. Under standard nomenclature used throughout this disclosure, the terminal portion of the designated side chain is described first followed by the adjacent functionality toward the point of attachment. For example, a $C_{1-6}$ alkyl substituted with $C_{1-5}$ alkylcarbonylamino is equivalent to

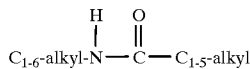

In the schemes and examples below, various reagent symbols have the following meanings:
BOC
(or Boc): t-butyloxycarbonyl
Pd-C: Palladium on activated carbon catalyst
DMF: Dimethylformamide
DMSO: Dimethylsulfoxide
CBZ: Carbobenzyloxy
$CH_2Cl_2$: Methylene chloride
$CH_2Cl_3$: chloroform
ETOH: ethanol
MeOH: methanol
EtOAc: ethyl acetate
HOAc: acetic acid
BOP: Benzotriazol-1-yloxytris (dimethylamino) phosphonium, hexafluorophosphate
EDC: 1-(3 -Dimethylaminopropyl)-3 -ethylcarbodiimide hydrochloride
Oxone: potassium peroxymonosulfate
LDA: Lithium diisopropylamide
PYCLU: Chloro -N,N,N',N'-bis (pentamethylene) formamidinium hexafluorophosphate The compounds of the present invention can be administered in such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but non-toxic amount of the compound desired can be employed as an anti-aggregation agent.

Compounds of the invention, or pharmaceutically acceptable salts thereof, are useful in the manufacture of a medicament for inhibiting binding of fibrinogen to the platelet membrane glycoprotein complex IIb/IIIa receptor, preventing platelet thrombosis, thromboembolism and reocclusion during and after thrombolytic therapy or after angioplasty or coronary artery bypass procedures, and preventing myocardial infarction in a mammal.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., Amer. J. Physiol., 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.01–100 mg/kg/day and most preferably 0.01–20 mg/kg/day. For example, a typical 90 kg patient would receive oral dosages ranging between about 0.9 mg/day and about 9 g/day, most preferably between about 0.9 mg/day and 1.8 g/day. Suitable pharmaceutical oral compositions such as tablets or capsules may contain, for example, 10 mg, 100 mg, 200 mg and 500 mg. Intravenously, the most preferred doses will range from about 1 to about 10 mg/kg/mlnute during a constant rate infusion.

Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdernmal delivery system, the dosage administration will, or course, be continuous rather that intermittent throughout the dosage regime.

In the methods of the present invention, the compounds herein described in detail are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the compound can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral prodrug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Active drug can also be co-administered with the usual doses of suitable anticoagulation agents, such as heparin or warfarin (typically given in tablet doses between 1 and 20 mg daily during administration of the active drug), or thrombolytic agents such as tissue plasminogen activator (typically given in i.v. doses of between 20 and 150 mg over two hour period prior to or during administration of the active drug), to achieve beneficial effects in the treatment of various vascular pathologies. Such co-administration also includes administration if the active drug with doses of anticoagulant agents or thrombolyric agents less than the usual doses of those agents.

Compounds of the invention may prepared according to a number of methods familiar to persons skilled in the art. For example, in one method, a fused, protected tricyclic ring system having a bromine substituent, e.g. 2-(1,1-Dimethylethoxycarbonyl)-7-bromo-1,2,3,4,-tetrahydro-9H-pyrido[3,4-b]indole, is converted to the corresponding carboxylic acid, e.g. 2-(1,1-Dimethylethoxycarbonyl)-1,2,3,4,-tetrahydro-9H-pyrido[3,4-<u>b</u>]indole-7-yl carboxylic acid, which is then combined with a 4-amino phenoxy compound, e.g. 1-(1,1-Dimethylethoxycarbonylamino)-2-(4-amino-3-methylphenoxy)ethane, to produce amine prodrugs of the invention.

In another general procedure, an isoindol carboxylic acid is reacted with 1,3-Diaminopropane to produce amine prodrugs of the invention.

In another general procedure, a protected 4-amino phenol, e.g. 4-amino-3-methylphenol , is converted to a phenoxyacetate with bromoacetate. The corresponding phenoxyacetamide is formed using dimethylamine. The phenoxyacetamide is reacted with a piperazinylbenzoic acid to form amine prodrugs of the invention.

These and other methods, including those exemplified below, may be used to prepare prodrugs of the invention.

EXAMPLE 1

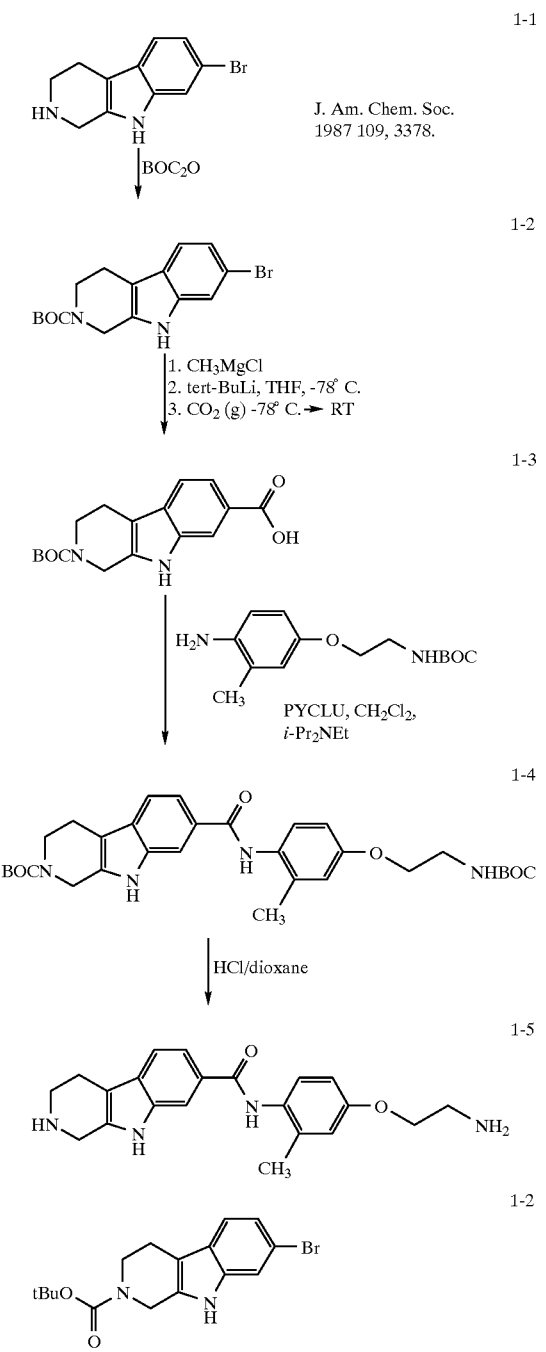

2-(1,1-Dimethylethoxycarbonyl)-7-bromo-1,2,3,4,-tetrahydro-9H-pyrido[3,4-b]indole 1-2

A suspension of 1-1, prepared by the method of Rinehart et al. (*J. Am. Chem. Soc.*, 1987 109, p 3378–3387)(0.366 g, 1.46 mmol) in $CH_2Cl_2$ (8 mL) was treated with triethylamine (0.61 mL, 4.4 mmol) followed by di-tert-butyldicarbonate (0.38 g, 1.7 mmol) for 1 hour at room temperature. The solution was concentrated and the residue chromatographed (20% EtOAc/hexanes) to give 1-2 as a white solid.

Rf (20% EtOAc/hexanes)=0.28 $^1$H NMR (400 MHz, CDCl$_3$) d 8.0–7.6 (m, 1H), 7.46 (s, 1H), 7.33 (d, 1H), 7.2 (d, 1H), 4.6 (bs, 2H), 3.78 (bs, 21H), 2.76 (bs, 2H), 1.5 (s, 9H).

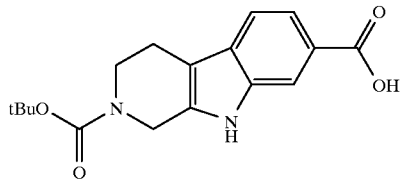

1-3

2-(1,1-Dimethylethoxycarbonyl)-1,2,3,4,-tetrahydro-9H-pyrido[3,4-b]indole-7-yl carboxylic acid 1-3

A solution of 1-2 (0.26 g, 0.734 mmol) in THF (10 mL) was cooled to 0° C. and treated with methylmagnesium chloride (3.0M in THF, 0.29 mL, 0.87 mmol) to give a pale yellow solution. After 15 minutes the solution was cooled to −78° C. and treated with t-BuLi (1.7M in pentane, 4.35 mL, 7.39 mmol) to give a bright yellow solution. After 10 minutes CO$_2$ gas was bubbled vigorously through the solution for 10 minutes. Saturated NH$_4$Cl, water and enough 6N NaOH to reach pH$_{12}$ were added and the solution extracted with EtOAc. The EtOAc layer was back extracted with 0.5 NaOH and the aqueous layers combined, acidified to pH 7 and extracted with EtOAc, the EtOAc layer was dried (Na$_2$SO$_4$) filtered and concentrated to give 1-3 as an off-white solid.

Rf (75:25:1 CHCl$_3$/MeOH/HOAc)=0.48 $^1$H NMR (400 MHz, DMSO-d6) d 12.0 bs, 1H), 11.2 (s, 1H), 7.93 (s, 1H), 7.6 (d, 1H), 7.45 (d, 1H), 4.6 (s, 2H), 3.68 (m, 2H), 2.7 (m, 2H), 1.4 (s, 9H).

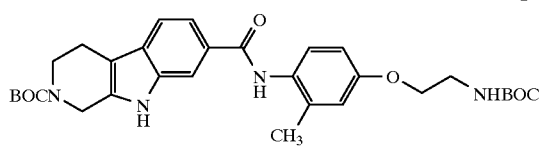

1-4

N-(3-Methyl-4-(2-(1,1-dimethylethoxycarbonylamino) ethoxy)phenyl)-7-(2-(1,1-dimethylethoxycarbonyl)-1,2,3, 4,-tetrahydro-9H-pyrido[3, 4-b]indol)carboxyamide 1-4

A solution of 1-3 (0.240 g, 0.759 mmol) and 4-6 (0.202 g, 0.758 mmol) in CH$_2$Cl$_2$ was treated with diisopropylethylamine (0.4 mL, 2.3 mmol) and PYCLU (0.304 g, 0.843 mmol) and stirred at room temperature for three days. The solution was concentrated and the residue was absorbed to silica gel and chromatographed in a gradient of 40 to 60% EtOAc/hexanes to give 1-4 as a white solid.

Rf (60% EtOAc/hexanes)=0.30; $^1$H NMR (400 MHz, CDCl$_3$) d 8.04 (s, 1H), 7.71 (d, 1H), 7.63 (s, 1H), 7.53 (s, 2H), 6.79 (s, 2H), 5.0 (s, 1H), 4.69 (s, 2H), 4.01 (t, 2H), 3.79 (t, 2H), 3.51 (d, 2H), 2.82 (t, 2H), 2.32 (s, 3H), 1.52 (s, 9H), 1.46 (s, 9H).

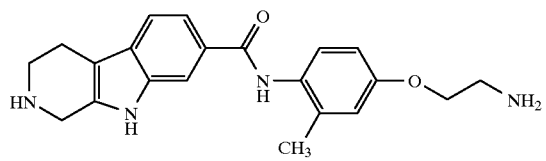

1-5

N-(3-Methyl-4-(2-aminoethoxy)phenyl)-7-(1,2,3,4,-tetrahydro-9H-pyrido[3,4-b]indol)carboxyamide 1-5

A solution of 1-4 in dioxane was cooled to 0° C. and treated with HCl (g) over 1.5 min. The mixture was stirred at 0° C. for 1 h and concentrated in vacuo. The residue was chromatographed (18:1:1 EtOH/H$_2$O/NH$_4$OH) to afford a white solid, which was then suspended in EtOAc and treated with HCl (g) to afford 1-5 as a white solid.

Rf (1 8:1:1 EtOH/H$_2$O/NH$_4$OH)=0.26; $^1$H NMR (400 MHz, D$_2$O) d 7.96 (s, 1H), 7.6 (m, 2H), 7.17 (d, 2H), 6.95 (s, 1H), 6.86 (d, 1H), 4.46 (s, 2H), 4.23 (t, 2H), 3.56 (t, 2H), 3.37 (t, 2H), 3.06 (t, 2H), 2.18 (s, 3H).

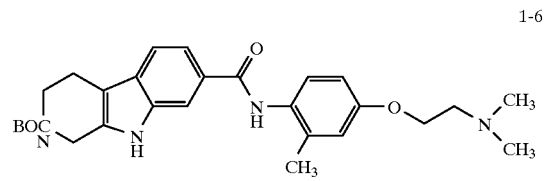

1-6

N-(3-Methyl-4-(2-(dimethylamino)ethoxy)phenyl)-7-(2-(1, 1-dimethylethoxycarbonyl)-1,2,3,4,-tetrahydro-9H-pyrido [3,4-b]indol)carboxyamide 1-6

1-3 (200 mg, 0.63 mmol) and 5-4 (0.63 mmol, 122 mg) were dissolved in methylene chloride. PYCLU (0.69 mmol, 250 mg) was added followed by DIPEA (2.52 mmol, 0.44 mL). The reaction was stirred at room temperature overnight. The reaction mixture was diluted with EtOAC and washed with H$_2$O, saturated NaHCO$_3$ and brine. The organic layer was dried (MgSO$_4$), filtered and concentrated to yield a tan solid. Flash chromatography (7% MeOH/CHCl$_3$ sat. NH$_3$) gave 1-6 as a yellow oil.

Rf (10% MeOH/CHNH$_3$ sat. Cl$_3$)=0.50; $^1$H NMR (400 MHz; CDCl$_3$) d 8.00 (bs, 1H); 7.52 (d, 1H); 7.48 (s, 1H); 7.5 (s, 1H); 6.51–6.55 (m, 3H); 4.61 (bs, 2H); 3.99–4.00 (t, 2H); 3.79–3.81 (bt, 2H); 2.79–2.81 (bt, 2H); 2.61–2.63 (t, 2H); 2.32 (s, 3H); 2.34 (s, 3H); 2.30 (s, 3H); 1.50 (s, 9H).

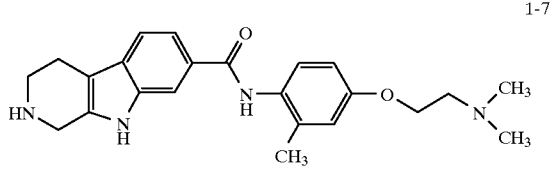

1-7

N-(3-Methyl-4-(2-(dimethylamino)ethoxy)phenyl)-7-(1,2, 3,4,-tetrahydro-9[H-pyrido[3,4-b]indol)carboxyamide 1-7

1-6 was dissolved in EtOAc and cooled to −78°. HCl (g) was bubbled through until the solution was saturated. The reaction mixture was warmed to 0° and stirred for 15 minutes. The reaction mixture was concentrated to yield a brown solid which was purified by flash chromatography (gradient 10% MeOH/CHCl$_3$ saturated with NH$_3$ to 60% MeOH/CHCl$_3$ saturated with NH$_3$)) to yield 1-7 as a white solid.

Rf (10% MeOFH/CHCl₃ sat. NH₃)=0.19; ¹H NMR (400 MHz; DMSO-d6) d 9.73 (s, 1H); 9.45–9.55 (bs, 1H); 8.05 (s, 1H); 7.69 (d, 1H); 7.57 (d, 1H); 7.24–7.26 (d, 1H); 4.40 (s, 2H); 4.35 (t, 2H); 3.47–3.5 (m, 4H); 2.99–3.1 (t, 2H); 2.50 (s, 6H); 2.22 (s, 3H).

EXAMPLE 2

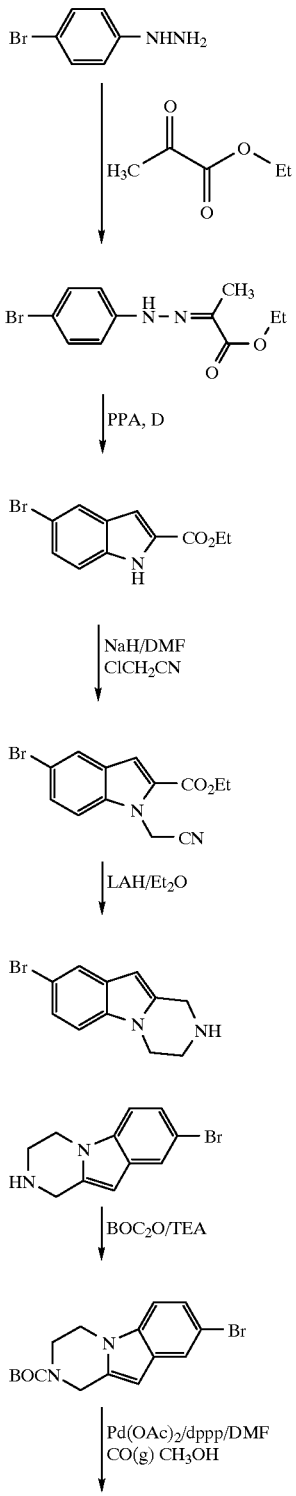

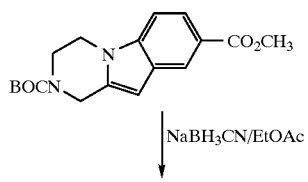

2-6

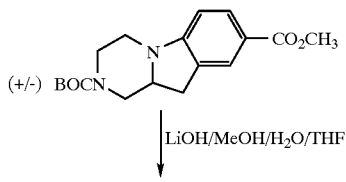

2-7

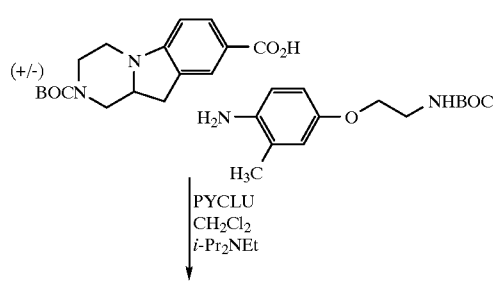

2-8

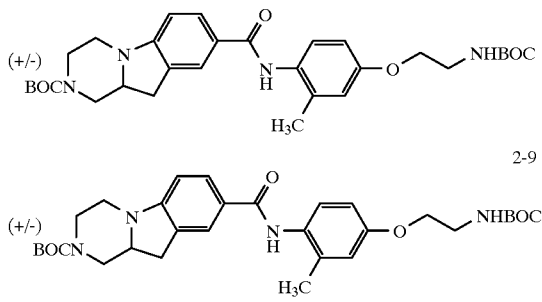

2-9

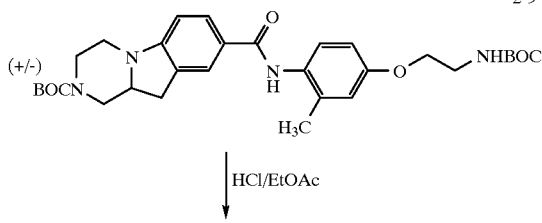

2-9

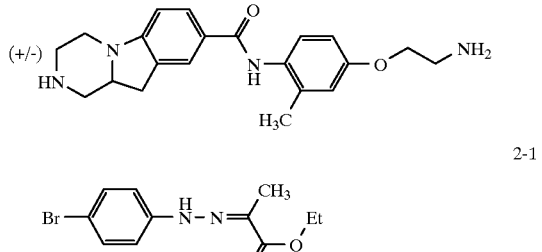

2-10

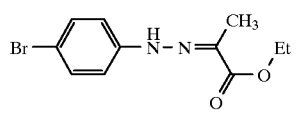

2-1

Ethyl 2-(4-bromo-1-hydrazinimine)propanoate 2-1

A mixture of 4-bromophenylhydrazine (Aldrich, 0.5 g, 2.2 mol) and ethyl acetoacetate (Aldrich, 0.24 mL, 2.2 mmol) in pyridine (0.6 mL) was heated to reflux overnight. The reaction was cooled, diluted with water and the precipitate that resulted was collected and washed with water, dried under vacuum to give 2-1.

Rf (10% MeOH/CHCl₃ saturated with NH₃)=0.86; ¹H NMR (400 MHz, CDCl₃) d 7.64 (s, 1H); 7.41 (d, 2H); 7.39 (d, 2H); 4.30–4.34 (q, 2H); 2.10 (s 3H); 1.36 (t, 3H).

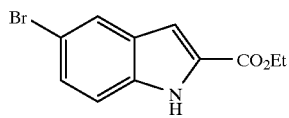

2-2

5-Bromo-2-ethoxycarbonyl indole 2-2

A mixture of 2-1 (0.54 g, 1.9 mmol) and polyphosphoric acid (1.6 mL) was heated to 115° C. for 10 minutes, then diluted with cold water and extracted with EtOAc. The layers were separated and the aqueous layer extracted with EtOAc. The organic layers were combined, washed with brine, dried with MgSO$_4$, filtered and concentrated to give 2-2 as a brown solid.

Rf (30% EtOAc/hexanes)=0.45; $^1$H NMR (400 MHz, CDCl$_3$) d 8.95(bs, 1H); 7.82 (s, 1H); 7.41 (d, 1H); 7.30 (d, 1H); 7.15 (s, 1H); 4.44 (q, 2H); 1.40 (t, 3H).

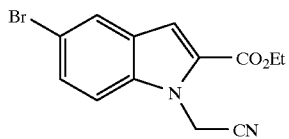

2-3

1-(Cyanomethyl)-2-ethoxycarbonyl-5-bromo-indole 2-3

A solution of 2-2 (11.2 g, 44.4 mmol) in DMF (400 mL) was treated with NaH (3.2 g of 60% dispersion in oil, 66.6 mmol) for 0.5 hour and then chloroacetonitrile (Aldrich, 5.6 mL, 88.8 mmol) was added and the reaction was stirred overnight. The solvent was removed in vacuo and the residue was partitioned between water and EtOAc. The water layer was extracted with EtOAc, the organic layers were combined, washed with water, brine, dried with MgSO$_4$, filtered and evaporated to give 2-3 as a brown solid.

Rf (30% EtOAc/hexanes)=0.46; $^1$H NMR (400 MHz, CDCl$_3$) d 7.82–7.83 (bs, 1H); 7.51–7.54 (dd, 1H); 7.30–7.32 (bd, 2H); 5.60 (s, 2H); 4.41–4.43 (q, 2H); 1.41–1.43 (t, 3H).

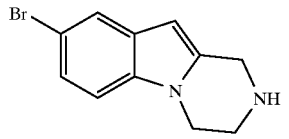

2-4

8-Bromo-2,3 4 5-tetrahydropyrazino-[1,2-a]indole 2-4

A slurry of 2-3 (12.2 g, 39.7 mmol) in diethyl ether (400 mL) was added via dropping funnel to a solution of LAH in ether (79.4 mL, 1M in ether, 79.4 mmol) and stirred at room temperature overnight. The slurry was diluted with saturated sodiumpotassium tartrate (Rochelle's salt) and stirred for 15 minutes, then transferred to a separatory funnel containing EtOAc and the layers separated. The aqueous layer was extracted with EtOAc, the organic layers were combined, washed with water, brine, dried with MgSO$_4$, filtered and evaporated to give 2-4 as a brown solid.

Rf (10% MeOH/CHCl)$_3$ saturated with NH$_3$)=0.42 $^1$H NMR (400 MHz, CDCl$_3$) d 8.38–8.41(bs, 1H); 7.66 (s, 1H); 7.2–7.22 (dd, 2H$_1$); 7.14 (d, 2H), 6.14 (s, 1H); 4.22 (s, 2H); 3.99 (t, 2H); 3.36–3.37 (t, 2H).

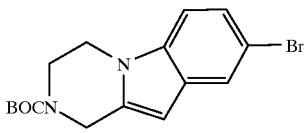

2-5

8-Bromo-3-(1,1-dimethylethoxycarbonyl)-2,3,4,5-tetrahydropyrazino-[1,2-a]indole 2-5

A solution of 2-4 (10 g, 40 mmol) in CH$_2$Cl$_2$ (200 mL) was cooled to 0° C. and treated with di-tertbutyldicarbonate (8.7 g, 40 mmol) and triethylamine (5.6 mL, 40 mmol). The solution was allowed to war slowly and after 48 hours was concentrated and the residue dissolved in EtOAc, washed with water and brine, dried over Na$_2$SO$_4$, filtered and evaporated. The residue was chromatographed (30% EtOAc/hexanes) to give 2-5 as a solid.

Rf (30% EtOAc/hexanes)=0.22; $^1$H NMR (400 MHz, CDCl$_3$) d 7.67 (d, 1H); 7.23 (d, 1H); 7.13 (d, 1H); 6.21 (s, 1H); 4.80 (s, 2H); 4.04 (t, 2H); 3.93 (t, 2H); 1.50 (s, 9H).

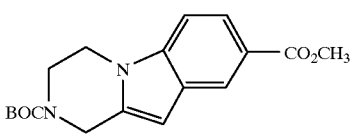

2-6

8-Methoxycarbonyl-3-(1,1-dimethylethoxycarbonyl)-2,3,4,5-tetrahydropyrazino-[1,2-a]indole 2-6

A solution of 2-5 (3.0 g, 8.5 mmol) in MeOH (60 mL) and DMSO (20 mL) was treated with triethylamine (3.55 mL, 25.5 mmol), 1,3-Bis(diphenylphosphino)propane (1.75 g, 4.25 mmol) and palladium (II) acetate (0.952 g, 4.25 mmol). Carbon monoxide was bubbled through the solution while it was heated to reflux for 2 hours. The reaction was heated at reflux overnight under a balloon atmosphere of carbon monoxide. Additional 1,3-Bis(diphenylphosphino)propane (0.8 g, 2.12 mmol) and palladium acetate (0.476 g, 2.12 mmol) were added and the reaction was heated at reflux for 48 hours under a balloon atmosphere of carbon monoxide. The reaction was cooled to room temperature, the residue was partitioned between water and EtOAc. The water layer was extracted with EtOAc, the organic layers were combined, washed with water, brine, dried with MgSO$_4$, filtered and evaporated. The residue was chromatographed (25% EtOAc/hexanes) to give 2-6 as a yellow solid.

Rf (30% EtOAc/hexanes)=0.21; $^1$H NMR (400 MHz, CDCl$_3$) d 8.32 (s, 1H); 7.90 (d, 1H); 7.26 (d, 1H); 6.38 (s, 1H); 4.83 (s, 2H); 4.12 (t, 2H); 3.96–3.93 (m, 5H); 1.50 (s, 9H).

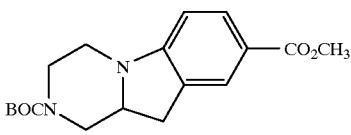

2-7

(+/−) 8-Methoxycarbonyl-3-(1,1-dimethylethoxycarbonyl)-1,1a,2, 3,4,5-hexahydropyrazino-[1,2-a]indole 2-7

2-6 (0.091 mmol, 30 mg) was dissolved in EtOAc and cooled to 0° C. NaBH$_3$CN (0.45 mmol, 28 mg) was added portion-wise and the reaction was warmed to room temperature for 15 min. The reaction mixture was basified with saturated NaHCO$_3$ and extracted into EtOAc. The organic layer was washed with brine, dried (MgSO$_4$), filtered and concentrated to yield 2-7 as a colorless oil.

Rf (2:1 hexane/EtOAc)=0.4; $^1$H NMR (400 MHz; CDCl$_3$) d 7.83–7.82 (d, 1H); 7.73 (s, 1H); 6.40–6.38 (d, 1H); 4.15–4.0 (bs, 2H); 3.85 (s, 3H); 3.60–3.56 (m, 2H); 0.305–2.65 (m, 4H); 2.60–2.58 (dd, 1H); 1.50 (s, 9H).

2-8

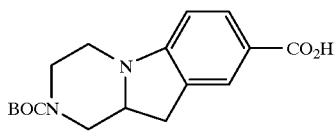

(+/−) 3-(1,1-Dimethylethoxycarbonyl)-1,1a,2,3,4,5-hexahydropyrazino-[1,2-a]indole-8-carboxylic acid 2-8

2-7 (0.90 mmol, 300 mg) was slurried in THF/H$_2$O/MeOH (2mL/2/2). LiOH (1.8 mmol, 76 mg) was added and the reaction mixture was heated to 50° C. After 0.5 hours, the reaction mixture became homogeneous, and was then stirred at room temperature for an additional 2 hours. The reaction mixture was diluted with 10% citric acid and EtOAc. The layers were separated, and the organic layer was washed with H$_2$O and brine. Drying (MgSO$_4$), filtering and concentrating gave 2-8 as a yellow solid.

Rf (97/3/1 CHCl$_3$/MeOH/HOAC)=0.70; $^1$H NMR (400 MHz; CDCl$_3$) d 7.90 (d, 1H); 7.87 (s, 1H); 6.4–6.39 (d, 1H); 4.25–4.0 (bs, 2H); 3.65–3.57 (m, 2H); 3.10–3.0 (dd, 1H); 3.02–2.98 d, 1H); 2.98–2.91 (bs, 1H); 2.69–2.66 (bs, 1H); 2.62–2.60 (dd, 1H); 1.50 (s, 9H).

2-9

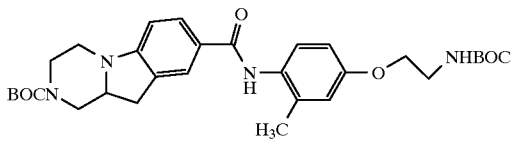

(+/−) N-(3-Methyl-4-(2-(1,1-dimethylethoxycarbonylamino)ethoxy)phenyl)-3-(1,1-dimethylethoxycarbony)-1,1a,2,3,4,5-hexahydropyrazino-[1,2-a]indole-8-carboxamide 2-9

2-8 (0.63 mmol, 200 mg) and 4-6 (0.63 mmol, 167 mg) were slurred in CH$_2$Cl$_2$. PYCLU (0.70 mmol, 252 mg) was added followed by Diisopropylethylamine (2.5 mmol, 0.44 mL). The slurry was stirred at room temperature overnight. The reaction mixture was diluted with EtOAc and washed with water and brine, dried (MgSO$_4$), filtered and concentrated to yield a tan solid. Flash chromatography (60% EtOAc/hexanes) gave 2-9 contaminated with bispiperidine urea by-product which was removed by triturations with ether.

Rf (70% EtOAc/hexanes)=0.50; $^1$H NMR (400 MHz; CDCl$_3$) 7.65–7.63 (m, 3H); 7.36 (s, 1H); 6.77–6.75 (m, 2H), 6.45–6.43 (d, 2H); 5.0 (s, 1H); 4.05–4.25 (bs, 2H); 4.02–3.99 (t, 2H); 3.60–3.57 (m, 4H); 3.05–2.63 (m, 4H); 2.63–2.59 (dd, 1H); 2.28 (s, 3H); 1.50 (s, 9H).

2-10

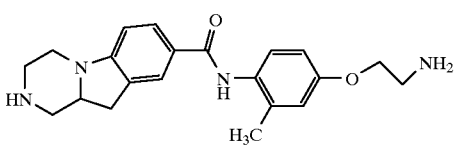

(+/−) N-(3-Methyl-4-(2-aminoethoxy)phenyl)-1,1a,2,3,4,5-hexahydropyrazino-[1,2-a]indole-8-carboxamide 2-10

2-9 (180 mg) was dissolved in EtOAc and cooled to −78° C. HCl(g) was bubbled through until the solution was saturated. The reaction mixture was stirred at 0° for I hour and then at room temperature for an additional hour. The reaction mixture was concentrated to yield a yellow solid which was purified by flash w chromatography (10/0.510.5 EtOH/NH$_4$OH/H$_2$O) to yield 2-10 as an off-white solid.

Rf (10/1/1 EtOH/NH$_4$OH/H$_2$O)=0.33; $^1$H NMR (400 MHz; DMSO-d$_6$) d 9.28 (s, 1H); 7.71–7.69 (d, 1H); 7.65 (s, 1H); 7.14–7.12 (d, 1H); 6.82–6.81 (d, 1H); 6.76–6.73 (dd, 1H); 6.50–6.48 (d, 1H); 3.92–3.89 (t, 2H); 3.62–3.57 (bd, 2H); 3.52–4.45 (m, 1H); 2.97–2.81 (m, 6H); 2.58–2.50 (t, 1H); 2.15 (s, 3H).

EXAMPLE 3

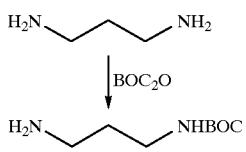

3-1

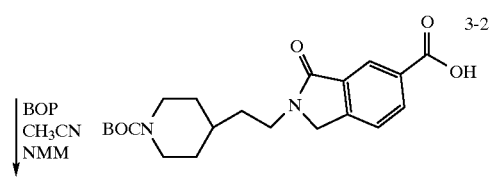

3-2

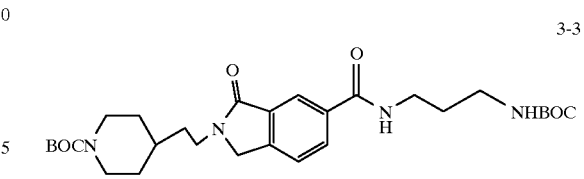

3-3

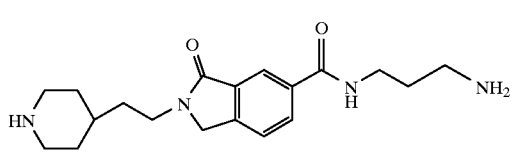

3-4

3-1

3-(1-Dimethylethoxycarbonylamino)propylamine 3-1

1,3-Diaminopropane [Aldrich] (40.5 mmol, 3.4 mL) was dissolved in CHCl$_3$ and cooled to 0° C. 1Di-tert-butyldicarbonate (13.5 mmol, 2.9 g) was added and the reaction mixture was stirred for two hours at 0° C. The reaction mixture was washed with 10% KHSO$_4$. The aqueous layers were combined, basified to pH$_{10}$ with saturated NaHCO$_3$, and extracted with EtOAc and CHCl$_3$. The organic layers were combined, dried (Na$_2$SO$_4$), filtered and concentrated to yield pure 3-1as a tan oil.

Rf (20% MeOH/CHCl$_3$ sat. NH$_3$)=0.3; $^1$H NMR (400 MHz; CDCl$_3$) d 5.0 (bs, 1H); 3.18–3.17 (bq, 2H); 2.75–2.71 (t, 2H); 1.68 (bs, 2H); 1.60–1.57 (m, 2H); 1.40 (s, 9H).

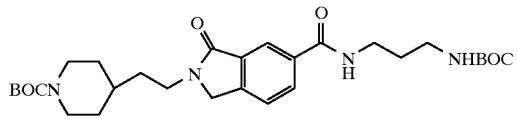

3-3

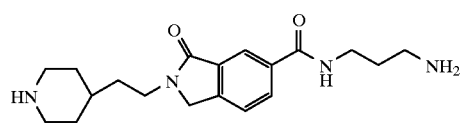

3-4

N-(3-(1,1-Dimethylethoxycarbonylamino)propyl)-2-((1-(1,1dimethylethyoxycarbonyl)piperidine-4-yl)ethyl)-1,3-dihydroisoindol-1-one-6-carboxamide 3-3

3-2 (Prepared as described in EP 0540334)(0.65 mmoL, 250 mg) and 3-1 (0.97 mmol, 167 mg) were slurried in CH₃CN. NMM (0.65 mmol, 0.079 mL) was added, followed by BOP reagent (0.84 mmol, 370 mg). The homogenous reaction mixture was stirred for 48 hours at room temperature. The reaction mixture was diluted with EtOAc and washed with water, 10% KHSO₄, saturated NaHCO₃, and brine. The organic layer was dried (MgSO₄), filtered and concentrated to yield an oil. Flash chromatography (gradient 50% EtOAc/hexanes to 100% EtOAc) yielded 3-3 as a yellow solid.

Rf (EtOAc)=0.45; $^1$H NMR (400 MHz, CDCl₃) d 8.21 (s, 1H); 8.13 (d, 1H); 7.54 (d, 1H); 4.95 (bt, 1H); 4.41 (s, 2H); 4.13–4.10 (bd, 2H); 3.70–3.65 (t, 2H); 3.54–3.51 (q, 2H); 3.25–3.23 (q, 2H); 2.67–2.64 (bt, 2H); 1.76–1.73 (m, 3H); 1.65–1.60 (m; 6H); 1.5 (s, 18H); 1.14–1.16 (q, 2H).

N-(3-aminopropyl)-2-(4-piperidinyl)ethyl-1,3-dihydroisoindol-1-one-6-carboxamide 3-4

3-3 was dissolved in EtOAc and cooled to −78° C. HCl(g) was bubbled through until the solution was saturated. The reaction was allowed to stir for 1 hour at 0°. The reaction mixture was then concentrated to yield pure 3-4 as a white solid.

Rf (10/1/1 EtOH/NH₄OH/H₂O)=0.93; $^1$H NMR (400 MHz; DMSO-d6) 8.6 (bd, 1H); 8.19 (s, 1H); 8.10 (d, 1H); 7.92 (bs, 2H); 7.77–7.69 (d, 1H); 4.55 (s, 2H); 3.58 (t, 2H); 3.23 (bd, 2H); 1.90–1.82 (m, 4H); 1.60–1.56 (m, 31H); 1.27–1.06 (m, 2H).

EXAMPLE 4

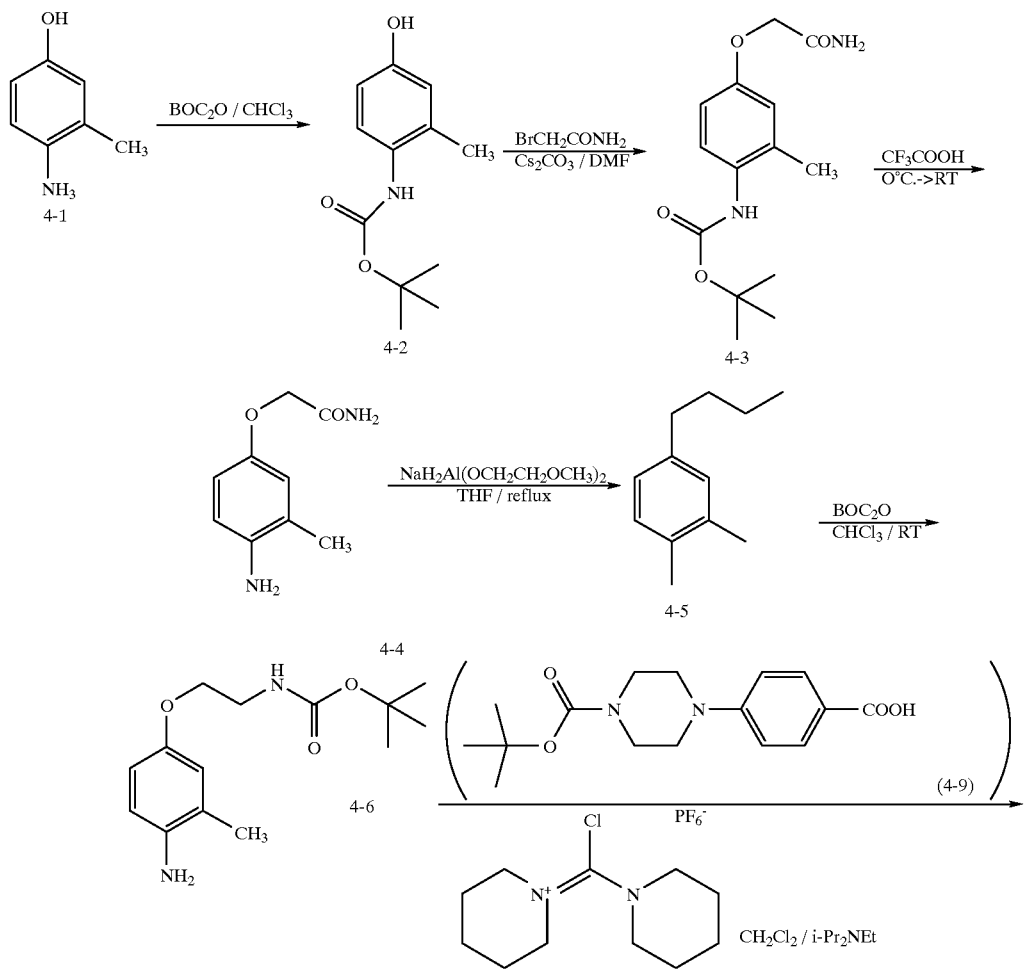

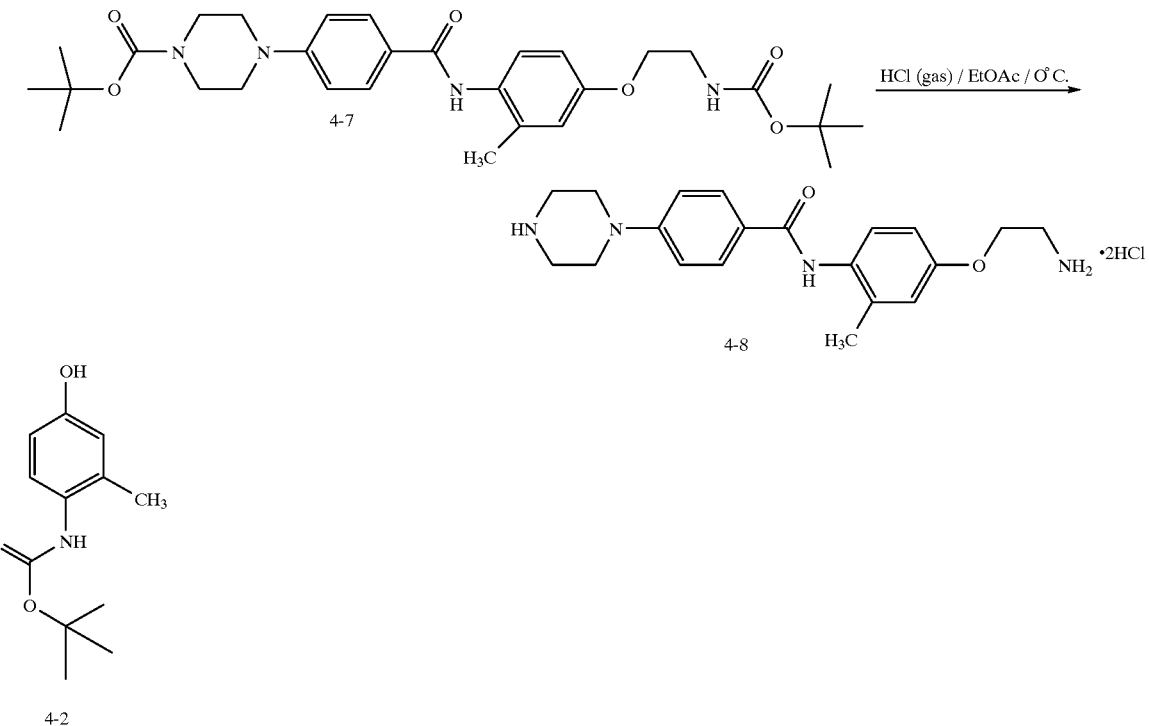

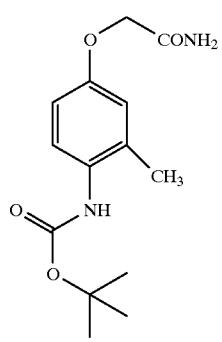

4-2

4-(1,1-Dimethylethoxycarbonyl)amino-3-methylphenol (4-2)

To a 1 L round bottomed flask with a stirring bar, reflux condenser and an argon inlet was added 4-amino-3-methylphenol (15.00 g, 121.79 mmol), di-tert-butyldicarbonate (27.25 g, 124.84 mmol) and CH$_2$Cl$_2$ (300 mL). This heterogeneous mixture was heated at reflux for 24 h during which time all of the solids dissolved. The mixture was cooled to room temperature and the solid product was collected by filtration. The material was triturated with a mixture of Et$_2$O-hexanes (1:1), collected on a frit and dried in vacuo to give 21.25 g (92%) of 4-(1,-dimethylethoxycarbonyl)amino-3-methylphenol (10-2), mp: 143–144° C.

$^1$H NMR (CDCl$_3$): d 1.51 (s, 9H), 2.14 (s, 3H), 6.08 (br s, 1H), 6.48 (m, 2H), 6.60 (br s, 1H), 7.20 (d, j=8.5 Hz, 1H).

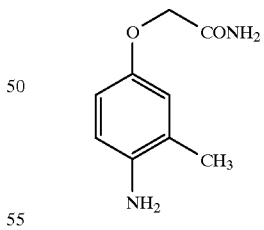

4-3

4-(1,1-Dimethylethoxycarbonyl)amino-3-methylphenoxyacetamide (4-3)

To a 200 mL round bottomed flask with a stirring bar, and an argon inlet was added 4-(1,1-dimethylethoxycarbonyl)amino-3-methylphenol (5.00 g, 22.39 mmot), Cs$_2$CO$_3$ (14.59 g, 44.78 mmol), DMF (50 mL), and bromoacetamide (3.24 g, 23.51 mmol). This mixture was stirred vigorously at ambient temperature for 24 h. The mixture was filtered through a frit and the DMF was removed under high vacuum. The residue was dissolved in EtOAc (300 mL) and washed wit H$_2$O (2×) and brine (1×). Drying (MgSO$_4$), filtration, and removal of the solvent in vacuo gave a solid. This material was triturated with EtOAc, the solid was collected by filtration and dried in vacuo to give 4.91 g (78%) of 4-(1,1-dimethyl-ethoxycarbonyl)amino-3-methylphenoxyacetamide as a white, crystalline solid.

$^1$H NMR (CDCl$_3$): d 1.50 (s, 9H), 2.22 (s, 3H), 4.42 (s, 2H), 5.81 (br s, 1H), 6.18 (s, 1H), 6.51 (br s, 1H), 6.78 (m, 2H), 7.58 (s, 1H).

4-Amino-3-methylphenoxyacetamide (4-4)

To a 200 m1L round bottomed flask with a stirring bar and an argon inlet was added 4-(1,1-dimethylethoxycarbonyl) amino-3-methylphenoxyacetamide (4.91 g, 17.52 mmol) and trifluoroacetic acid (50 mL). This solution was stirred at 0° C. for 5 h. The trifluoroacetic acid was removed in vacuo and the residue was partitioned between EtOAc and aqueous NaHCO$_3$ solution. The layers were separated and the organic phase was washed with brine, dried (MgSO$_4$), filtered and concentrated in vacuo to give 1.60 g of 4-amino-3-methylphenoxy-acetamide as a white solid.

$^1$H NMR (CDCl$_3$): d 2.18 (s, 31H), 3.41 (br s, 21H), 4.40 (s, 2H), 5.71 (br s, 1H), 6.61 (s, 2H), 6.64 (s, 1H).

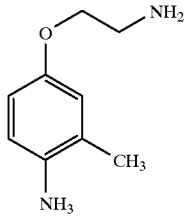

4-5

2-(4-Amino-3-methylphenoxy)ethylamine (4-5)

To a 200 mL round bottomed flask with a stirring bar, reflux condenser and an argon inlet was added 4-amino-3-methylphenoxyacetamide (1.60 g, 8.88 mmol) and dry THF (100 mL). To this solution was added a solution of sodium bis(2-methoxyethoxy)aluminium hydride (10.0 mL of a 3.4M solution in toluene, 6.87 mmol). This solution was heated at reflux for 4 h. The cooled reaction mixture was treated with saturated aqueous sodium potassium tartrate solution and extracted with EtOAc. The combined EtOAc extracts were dried (MgSO$_4$), filtered and concentrated in vacuo. The crude 2-(4-amino-3-methylphenoxy)ethylamine was used in the next step without further purification.

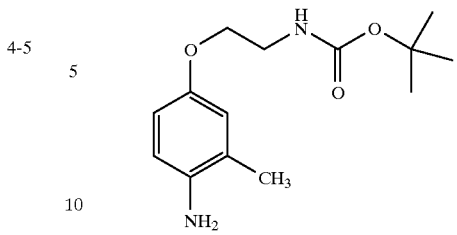

4-6

1-(1,1-Dimethylethoxycarbonylamino)-2-(4-amino-3-methylphenoxy)ethane (4-6)

To a 100 mL round bottomed flask with a stirring bar and an argon inlet was added 2-(4-amino-3-methylphenoxy)ethylamine (0.997 g, 6.00 mmol), chloroform and di-tert-butyldicarbonate (1.31 g, 6.00 mmol). This solution was stirred at ambient temperature 2 h. The solvent was removed in vacuo and the residue was chromatographed on 75 g of silica gel using EtOAc-hexane (2:3) as eluant. There was obtained 1.56 g (98%) of 1-(1,1-dimethylethoxycarbonylamino)-2-(4-amino-3-methylphenoxy)ethane as a white crystalline solid. $^1$H NMR (CDCl$_3$): d 1.42 (s, 9H), 2.19 (s, 3H), 3.35 (m, 2H), 3.48 (m, 21H), 3.92 (m, 2H), 4.98 (br s, 1H), 6.60 (s, 2H), 6.63 (s, 1H).

Preparation of 4-9

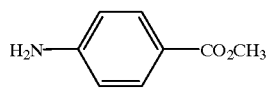

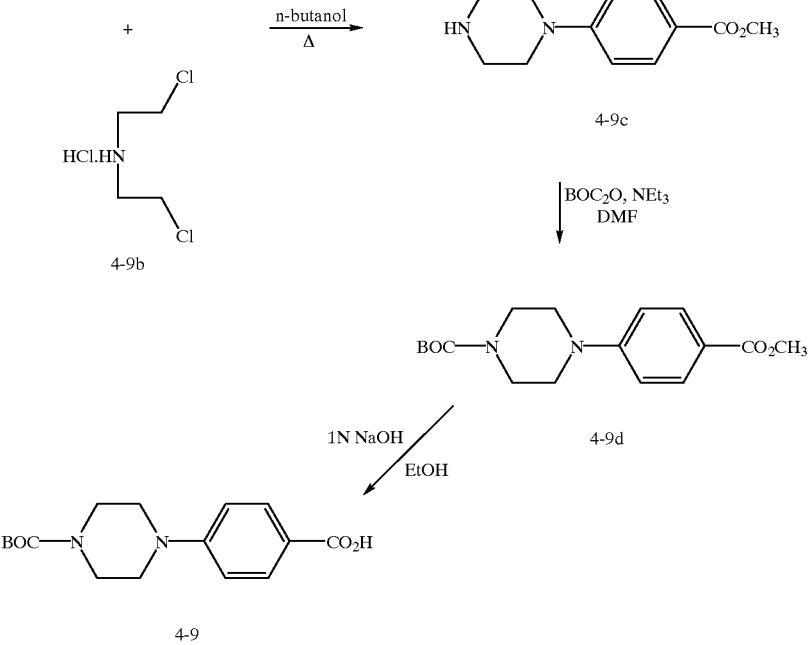

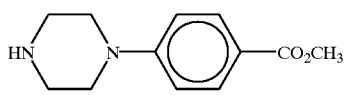

4-9c

4-(N-Piperazine)benzoic acid methyl ester (4-9c)

A solution of amine 4-9a (20.0 g, 132 mmol), amine 4-9b (23.6 g, 132 mmol) and n-butanol (500 ml) was refluxed for 168 h. The solution was allowed to cool to ambient temperature. The crystals were collected, washed with Et$_2$O and dried in vacuo to give ester 4-9c as a white solid.

$^1$H NMR (CD$_3$OD): δ 7.86 (d, J=9 Hz, 2H), 7.98 (d, J=9Hz, 2H), 3.78 (s, 3H), 3.53 (m, 4H), 3.31 (m, 4H).

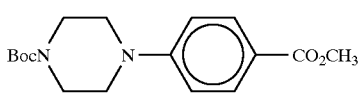

4-9d

4-(N-Boc-Piperazine)benzoic acid methyl ester (4-9d)

To a stirred solution of amine 4-9c (15.0 g, 61.1 mmol), NEt$_3$ (7.42 g, 73.4 mmol) and DMF (150 ml) was added Boc$_2$O (14.7 g, 67.2 mmol). After 1.0 h, the solution was diluted with EtOAc and then washed with H$_2$O, 10% KHSO$_4$, brine, dried (MgSO$_4$) and concentrated to furnish ester 4-9d as a yellow solid.

TLC Rf=0.63 (silica, 40% EtOAc/hexanes) $^1$H NMR (CD$_3$OD): δ 7.91 (d, J=9 Hz, 21H), 7.01 (d, J=9 Hz, 2H), 3.88 (s, 3H), 3.59 (m, 4H), 3.38 (m, 4H).

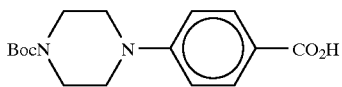

4-9

4-(N-Boc-Piperazine)benzoic acid (4-9)

A solution of ester 1-4 (21.1 g, 61.1 mmol) 1N NaOH (100 ml, 100 mmol) and EtOH (200 ml) was heated to 60° C. for 2.0 h. The solution was acidifed with 10% KHSO$_4$ and then extracted with EtOAc. The EtOAc phase was washed with brine, dried (MgSO$_4$) and concentrated to furnish acid 4-9 as a white solid.

$^1$H NMR (CD$_3$OD): δ 7.81 (d, J=9 Hz, 2H), 6.88 (d, J=9 Hz, 2H), 3.49 (m, 4H), 3.24 (m, 4H), 1.40 (s, 9H).

piperazin-1-yl)benzoic acid (0.863 g, 2.82 mmol), 1-(1,1-dimethylethoxycarbonylamino)-2-(4-amino-3-methylphenoxy)ethane (0.75 g, 2.82 mmol), chloro-N,N,N',N',-bis(pentamethylene)formamidinium hexafluorophosphate (1.068 g, 2.96 mmol) and CH$_2$Cl$_2$ (30 mL). When all of the solids had dissolved diisopropylethylamine (1.57 mL, 9.00 mol) was added. The resulting mixture was stirred at ambient temperature for 48 h. The mixture was diluted with CHCl$_3$ and washed with 10% aqueous citric acid, NaHCO$_3$ solution and brine. Drying (MgSO$_4$), filtration and removal of the solvent in vacuo gave the crude product. This material was chromatographed on 75 g of silica gel using EtOAc/hexane as eluant (1:1). There was obtained a white solid. This material was recrystallized from hot EtOAc-hexane to give 0.914 g (58%) of N-(2-methyl-4-(2-(1,1-dimethylethoxycarbonytamino)ethoxy)phenyl)-4-(4-(1,1-dimethylethoxycarbonyl)piperazin-1-yl)benzamide as white crystals. mp: 145–146° C. $^1$H NMR (CDCl$_3$): d 1.46 (s, 9H), 1.49 (s, 9H), 2.28 (s, 3H), 3.28 (m, 2H), 3.51 (s, 1H), 3.58 (m, 2H), 4.02 (m, 1H), 4.98 (br s, 1H), 6.76 (s, 2H), 6.93 (d, j=9 Hz, 2H), 7.43 (s, 1H), 7.66 (br s, 1H), 7.78 (d, j=9 Hz, 2H).

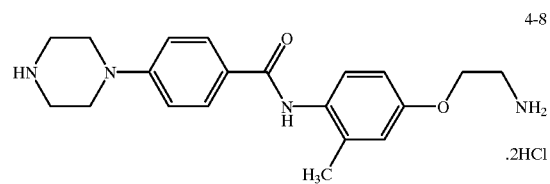

4-8

N-(2-Methyl-4-(2-aminoethoxy)phenyl)-4-(1-piperazinyl)benzamide, dihydrochloride (4-8)

To a 200 mL round bottomed flask with a stirring bar and a gas dispersion tube was added N-(2-methyl-4-(2-(1,1-dimethylethoxycarbonylamino)ethoxy)phenyl)-4-(4-(1,1-dimethylethoxycarbonyl)piperazin-1-yl)benzamide (0.912 g, 1.64 mmol) and 100 mL of dry EtOAc. This well stirred solution was cooled in an ice bath and saturated with HCl gas over 15 min. The mixture was aged 1 h at 0° C. and the excess HCl was then removed with a stream of argon. The EtOAc was removed in vacuo and the crude product was recrystallized from MeOH-EtOAc to give 0.70 g of N-(2-

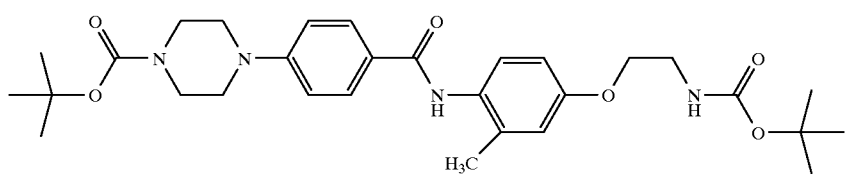

4-7

N-(2-Methyl-4-(2-(1,1-dimethylethoxycarbonylamino)ethoxy)phenyl)-4-(4-(1,1-dimethylethoxycarbonyl)piperazin-1-yl)benzamide (4-7)

To a 100 mL round bottomed flask with a stirring bar and an argon inlet was added 4-(4-(1,1-dimethylethoxycarbonyl)

methyl-4-(2-aminoethoxy)phenyl)-4-(1-piperazinyl)benzamide, dihydrochlorlide as a white solid. mp:>250° C. $^1$H NMR (CD$_3$OD): d 2.27 (s, 3H), 3.29 (m, 1H), 3.30 (m, 6H), 3.57 (m, 4H), 4.24 (t, j=5 Hz, 3H), 6.87 (dd, j=5,9 Hz, 1H), 6.94 (d, j=5 Hz, 1H), 7.12 (d, j=9 Hz, 2H), 7.22 (d, j=9 Hz, 1H), 7.91 (d, j=$^9$ Hz, 2H).

EXAMPLE 5
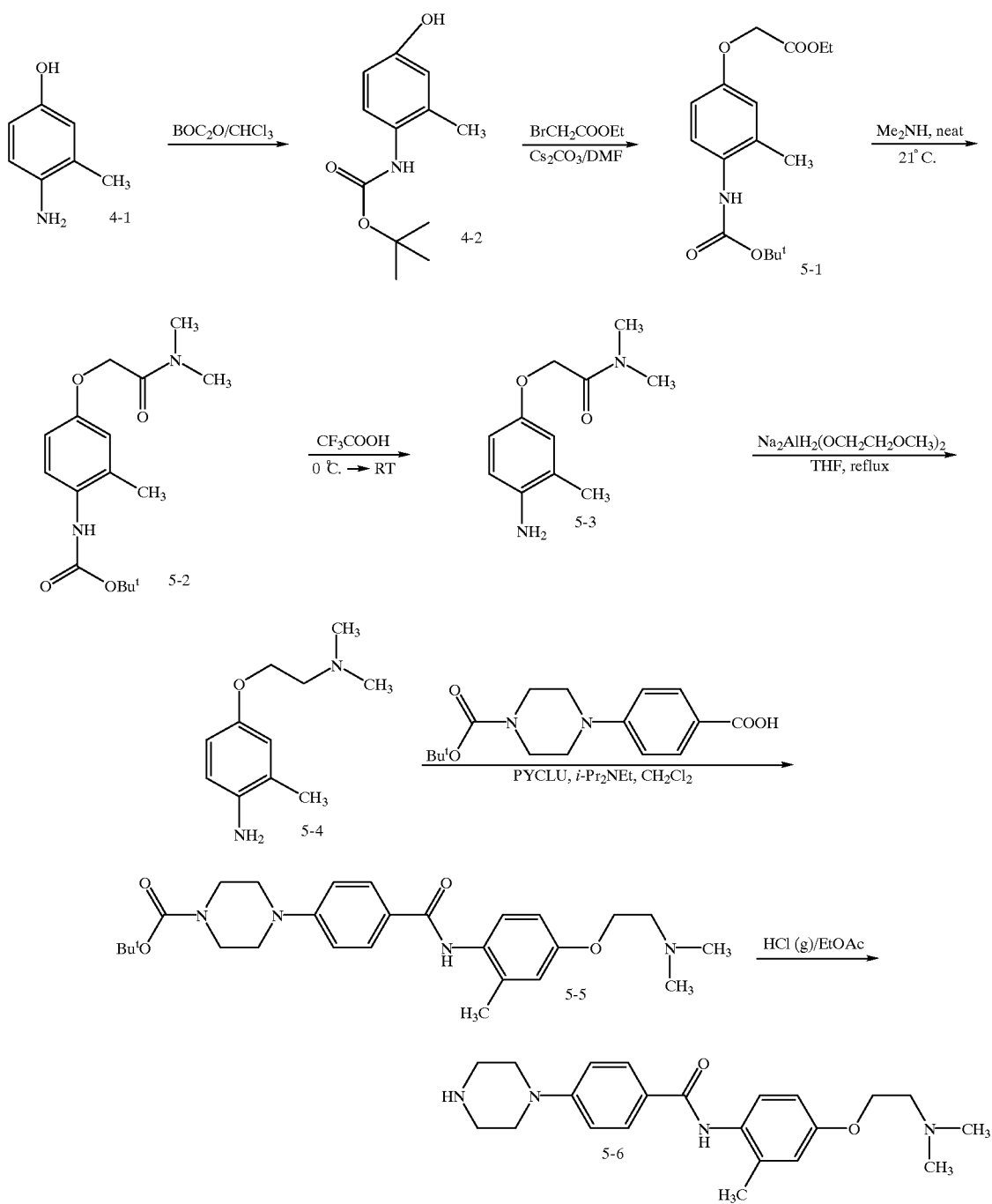

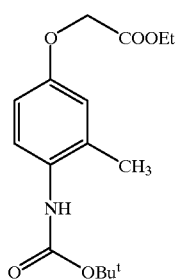

5-1

Ethyl 4-(1,1-dimethylethoxycarbonyl)amino-3-methylphenoxyacetate (5-1)

To a 200 mL round bottomed flask with a stirring bar, and an argon inlet was added 4-(1,1-dimethylethoxycarbonyl)amino-3-methylphenol (5.00 g, 22.39 mmol), Cs₂CO₃ (14.59 g, 44.78 mmol), DMF (50 mL), and ethyl bromoacetate (2.61 mL, 23.51 mmol). This mixture was stirred vigorously at ambient temperature for 24 h. The mixture was filtered through a frit and the DMF was removed under high vacuum. The residue was dissolved in EtOAc (300 mL) and washed with H₂O (2×) and brine (1×). Drying (MgSO₄), filtration, and removal of the solvent in vacuo gave a solid. This material was triturated with 5% Et₂O-hexane, the solid was collected by filtration and dried in vacuo to give 5.40 g (78%) of ethyl 4-(1,1-dimethylethoxycarbonyl)amino-3-methylphenoxyacetate as a white, crystalline solid.

¹H NMR (CDCl₃): d 1.29 (t, j=7.2 Hz, 3H), 1.51 (s, 9H), 2.22 (s, 3H), 4.26 (q, j=7.2 Hz, 2H), 4.57 (s, 2H), 6.08 (br s, 1H), 6.72 (m, 2H), 7.56 (s, 1H).

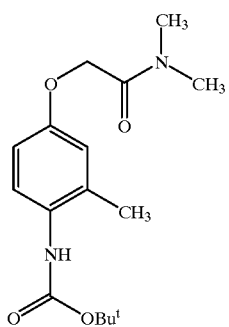

5-2

N,N-Dimethyl 4-(1,1-dimethylethoxycarbonyl)amino-3-methylphenoxyacetamide (5-2)

To a 100 mL pressure vessel with a stirring bar was added ethyl 4-(1,1-dimethylethoxycarbonyl)amino-3-methylphenoxyacetate (1.00 g, 3.24 mmol). The vessel was cooled in a Dry Ice®/2-propanol bath to −78° C. and dimethylamine was condensed onto the solid to a final volume of ~30 mL. The reaction vessel was sealed, allowed to warm to ambient temperature and stirred for 13 days. The excess dimethylamine was vented and the residue was dissolved in CHCl₃ and concentrated, twice to remove the last traces of dimethylamine. The crude product was chromatographed on 75 g of silica gel using 75/25 EtOAC-hexane as eluant to provide 1 g (100% yield) N,N-dimethyl-4-(1,1-dimethylethoxycarbonyl)amino-3-methylphenoxyacetamide as a white, crystalline solid. ¹H NMR (CDCl₃): d 1.50 (s, 9H), 2.22 (s, 3H), 2.96 (s, 3H), 3.07 (s, 3H), 4.63 (s, 2H), 6.09 (br s, 1H), 6.77, (s, 2H), 7.52 (br s, 1H).

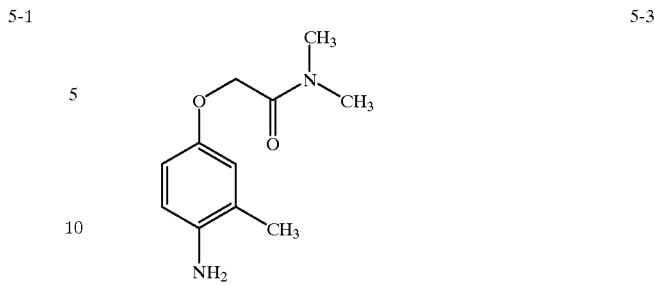

5-3

N,N-Dimethyl 4-amino-3-methylphenoxyacetamide (5-3)

To a 200 mL round bottomed flask with a stirring bar and a drying tube was added N,N-dimethyl 4-(1,1-dimethylethoxycarbonyl)amino-3-methyphenoxyacetamide (1.00 g, 3.24 mmol) and trifluoroacetic acid (20 mL). This solution was stirred at ambient temperature 48 h. The trifluoroacetic acid was removed in vacuo and the residue was dissolved in 200 mL of EtOAc. This solution was washed with NaHCO₃ solution and brine. Drying (MgSO₄), filtration and removal of the solvent in vacuo gave 0.493 g (73% yield) of N,N-dimethyl 4-amino-3-methylphenoxyacetamide as white crystals. ¹H NMR (CDCl₃): d 2.15 (s, 3H), 2.97 (s, 3H), 3.08 (s, 3H), 3.27 (br s, 2H), 4.59 (s, 2H), 6.71 (m, 3H).

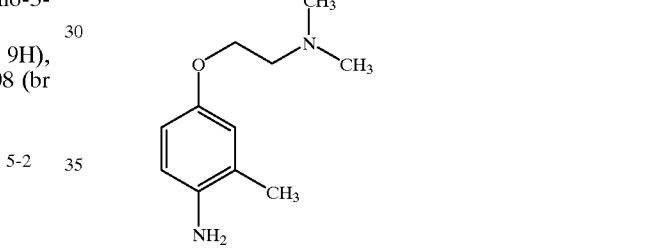

5-4

N,N-Dimethyl-2-(4-amino-3-methylphenoxy)ethylamine (5-4)

To a 200 mL round bottomed flask with a stirring bar, reflux condenser and an argon inlet was added N,N-dimethyl-4-amino-3-methylphenoxyacetamide (0.493 g, 2.37 mmol) and dry THF (20 mL). To this solution was added a solution of sodium bis(2-methoxyethoxy) aluminium hydride (2.78 mL of a 3.4M solution in toluene, 9.47 mmol). This solution was heated at reflux for 3 h. The cooled reaction mixture was treated with saturated aqueous sodium potassium tartrate solution and extracted with EttOAc. The combined EtOAc extracts were dried (MgSO₄), filtered and concentrated in vacuo. The crude N,N-dimethyl-2-(4-amino-3-methylphenoxy)ethylamine was used in the next step without further purification.

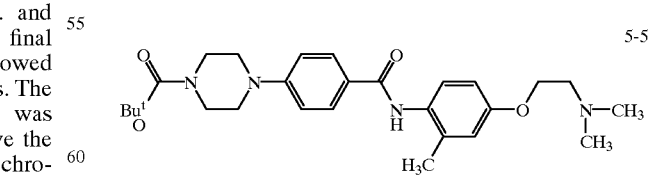

5-5

N-(2-Methyl-4-(2-(N,N-dimethylamino)ethoxy)phenyl)-4-(4-(1,1-dimethylethoxycarbonyl)piperazin-1-yl)benzamide (5-5)

To a 100 mL round bottomed flask with a stirring bar and an argon inlet was added 4-(4-(1,1-dimethylethoxycarbonyl)

piperazin-1-yl)benzoic acid (0.726 g, 2.37 mmol), N,N-dimethyl-2-(4-amino-3-methylphenoxy)ethylamine (0.46 g, 2.37 mmol), chloro-N,N,N',N',-bis(pentamethylene)formamidinium hexafluorophosphate (0.937 g, 2.60 mmol) and $CH_2Cl_2$ (30 mL). When all of the solids had dissolved diisopropylethylamine (1.57 mL, 9.00 mmol) was added. The resulting mixture was stirred at ambient temperature for 48 h. The mixture was diluted with $CHCl_3$ and washed with 10% aqueous citric acid, $NaHCO_3$ solution and brine. Drying ($MgSO_4$), filtration and removal of the solvent in vacuo gave a the crude product. This material was chromatographed on 75 g of silica gel using 2.5% 2-propanol in ammonia saturated $CHCl_3$ as eluant. There was obtained 0.45 g of a white solid. This material was tritutrated with $Et_2O$ and collected on a frit to give 0.300 g of N-(2-methyl-4-(2-(N,N-dimethyl-amino)ethoxy)phenyl)-4-(4-(1,1-dimethylethoxycarbonyl)piperzin-1-yl)benzamide as white crystals. $^1H$ NMR ($CDCl_3$): d 1.46 (s, 9Hz), 2.28 (s, 3H), 2.69 (s, 6H), 2.2.71 (t, j=6 Hz, 2H), 3.28 (m, 4H), 3.59 (m, 4H), 4.07 (t, j=6 Hz, 2H), 6.76 (s, 2H), 6.93 (d, j=9 Hz, 2H), 7.43 (s, 1H), 7.66 (br s, 1H), 7.78 (d, j=9 Hz, 2H).

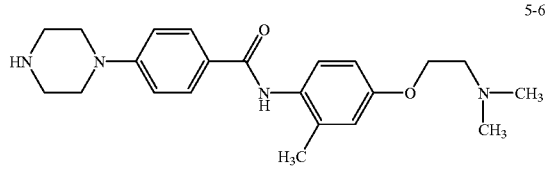

5-6

N-(2-Methyl-4-(2-(N,N-dimethyl)aminoethoxy)phenyl)-4-(1-piperazinyl)benzamide (5-6)

To a 200 mL round bottomed flask with a stirring bar and a gas dispersion tube was added N-(2-methyl-4-(2-(N,N-dimethylamino)ethoxy)phenyl)-4-(4-(1,1-dimethylethoxycarbonyl)piperazin-1-yl)benzamide (0.295 g, 0.61 mmol) and 50 mL of dry EtOAc. This well stirred solution was cooled in an ice bath and saturated with HCl gas over 15 min. The mixture was aged 1 h at 0° C. and the excess HCl was then removed with a stream of argon. The EtOAc was removed in vacuo and the crude product was partitioned between EtOAc and $NaHCO_3$ solution. The layers were separated, the organic phase was washed with brine and dried ($MgSO_4$). Filtration, removal of the solvent in vacuo and recrystallization from EtOAc gave 0.145 g of N-(2-methyl-4-(2-(N,N-dimethyl)aminoethoxy)phenyl)-4-(1-piperazinyl)benzamide, as a white crystals. mp: 139–141° C. $^1H$ NMR ($CDCl_3$): d 1.66 (br s, 1H), 2.28 (s, 3H), 2.33 (s, 6H), 2.72 (t, j=6 Hz, 2H), 3.05 (m, 4H), 3.27 (m, 4H), 4.05 (t, j=6 Hz, 2H), 6.77 (m, 2H), 6.93 (d, j=9 Hz, 2H), 7.45 (s, 1H), 7.63 (d, j=9 Hz, 1H), 7.77 (d, j=9 Hz, 2H).

EXAMPLE 6

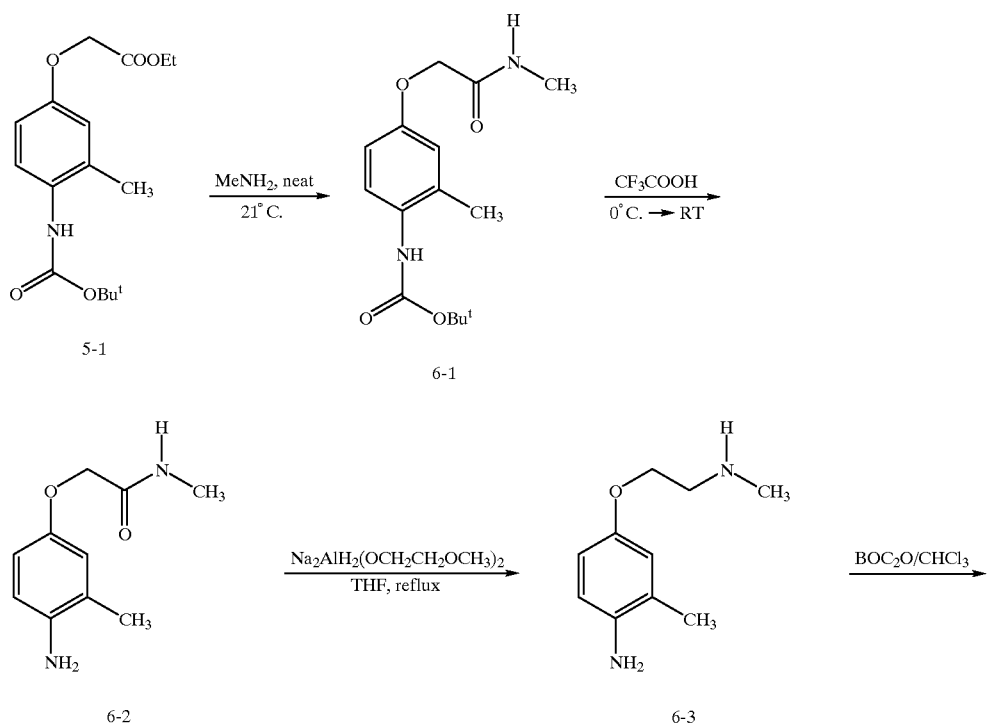

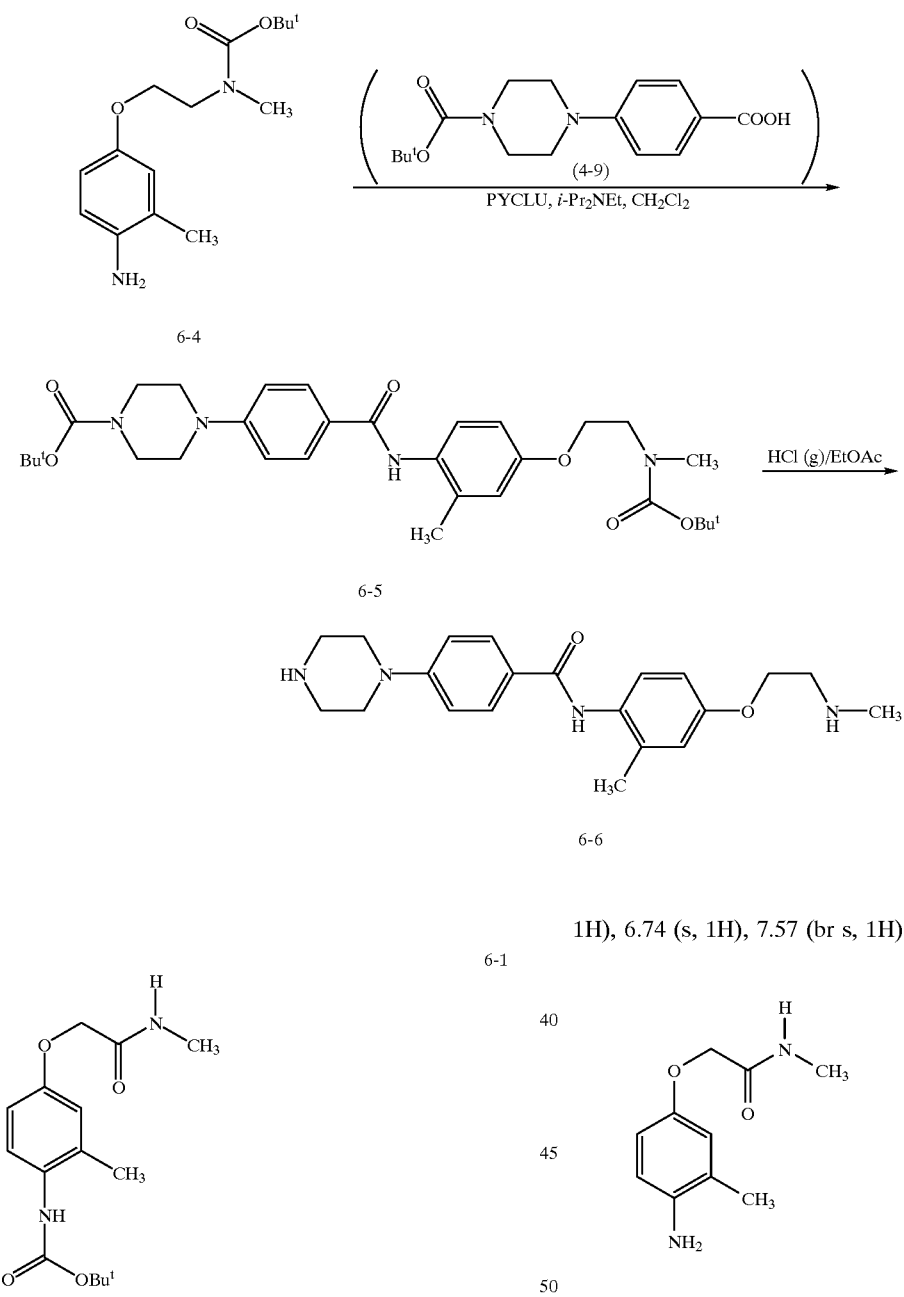

N-Methyl-4-(1,1-dimethylethoxycarbonyl)amino-3-methylphenoxyacetamide (6-1)

To a 50 mL glass pressure vessel with a stirring bar was placed 4-(1,1-dimethylethoxycarbonyl)amino-3-methylphenoxyethyl-ethoxycarbonyl (3.00 g, 9.7 mol). The vessel was cooled to −78° C. in a dry ice/acetone bath. 25 mL of methylamine was condensed into the vessel and was sealed with a screw cap. Ice bath was removed and the mixture was stirred at ambient temperature 48 h. The excess methylamine was evaporated and the residue was dissolved in $CHCl_3$ then concentrated in vacuo to remove traces of methylamine. Triturated the solid with $Et_2O$. Collected by filtration to give 2.65 g (94%) of the title compound above as a white crystalline solid.

$^1$H NMR ($CDCl_3$): d 1.5 (s, 9H), 2.23 (s, 3H), 2.90 (s, 3H), 4.45 (s, 2H), 6.09 (br s, 1H), 6.55 (br s, 1H), 6.72 (s, 1H), 6.74 (s, 1H), 7.57 (br s, 1H).

N-Methyl-2-(4-amino-3-methylphenoxy)acetamide (6-2)

To a 100 mL round bottomed flask with a stirring bar and an argon inlet was added N-methyl-4-(1,1-dimethylethoxycarbonyl)amino-3-methylphenoxyacetamide (2.5 g, 8.49 mmol) and trifluoroacetic acid (25 mL). This solution was stirred at 0° C. initially for 30 min then was warmed to room temperature and stirred 18 h. The trifluoroacetic acid was removed in vacuo and the residue was partitioned between EtOAc and aqueous $NaHCO_3$ solution. The layers were separated and the organic phase was washed with water and brine, dried ($MgSO_4$), filtered and concentrated in vacuo to afford 1.43 g of the title compound above as a brown oil.

$^1$H NMR ($CDCl_3$): d 2.15 (s, 3H), 2.90 (m, 3H), 4.41 (s, 2H), 6.61 (s, 2H), 6.66 (s, 1H).

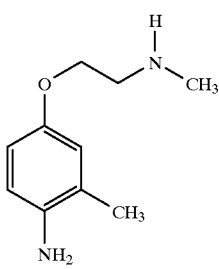

2-(4-Amino-3-methylphenoxy) N-methylethylamine (6-3)

To a 100 mL round bottomed flask with a stirring bar, refluxed condenser and an argon inlet was added N-methyl-2-(4-amino-3-methylphenoxy)acetamide(1.43 g, 7.36 mmol) and dry THF (50 mL). To this solution was added a solution of sodium bis(2-methoxy)aluminum hydride (7.57 mL of a 3.4M solution in toluene, 25.76 mmol). This suspension was heated to reflux for 3 h. The cooled solution was quenched with saturated aqueous sodium potassium tartrate solution and extracted with EtOAc (2×). Combined EtOAc layers were washed with water and brine. Dried (MgSO$_4$), filtered and in vacuo to give a crude brown oil which was chromatographed on silica gel using 5% IPA/NH$_3$ saturated CHCl$_3$ as eluant. Collected 0.61 g of a brown oil as the title compound above.

$^1$H NMR (CDCl$_3$): d 2.15 (s, 3H), 2.49 (s, 3H), 2.92 (t, j=5 Hz, 2H), 3.35 (br s, 2H), 3.99 (t, j=5 Hz, 2H), 6.62 (s, 21H), 6.67 (s, 1H).

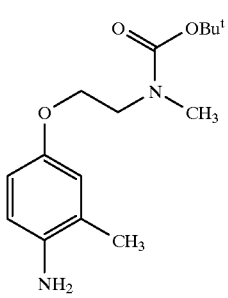

N-Methyl-N-(1,1-dimethylethoxycarbonyl)-2-(4-amino-3-methylphenoxy)ethylamine (6-4)

To a 100 mL round bottomed flask with a stirring bar and argon inlet was added 2-(4-amino-3-methylphenoxy) N-methylethylamine (0.600 g, 3.33 mmol), CHCl$_3$ (35 mL) and di-ter-butyldicarbonate (0.726 g, 3.33 mmol). The solution was stirred at ambient for overnight. The solvent was removed in vacuo. The crude N-methyl-N-(1,1-dimethylethoxycarbonyl)-2-(4-amino-3-methylphenoxy) ethylamine was used without further purification.

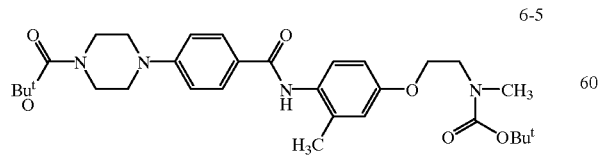

N-(2-Methyl-4-(2-(1,1-dimethylethoxycarbony(methyl) amino)ethoxy)phenyl)-4-(4-(1,1-dimethylethoxycarbonyl) piperazin-1-yl)benzamide (6-5)

To a 100 mL round bottomed flask with a stirring bar and an argon inlet was added 4-(4-(1,1-dimethylethoxycarbonyl) piperazine-1-yl)benzoic acid (0.5 g, 1.63 mmol), N-methyl-N-(1,1-dimethylethoxycarbonyl)-2-(4-amino-3-methylphenoxy)ethylamine (0.37 g, 1.32 mmol), chloro-N,N,N',N'-bis(pentamethylene)formamidinium hexafluorophosphate (0.625 g, 1.73 mmol) and CH$_2$Cl$_2$ (30 mL). To the mixture solution was then added diisopropyl-ethylamine (1.0 mL, 5.8 mmol). The resulting solution was stirring at room temperature for 24 h. Removed solvent in vacuo. Partitioned the residue between EtOAc and 10% aqueous citric acid, NaH$_2$CO$_3$ solution and brine. Dried (MgSO$_4$), filtration and removal of solvent in vacuo gave a crude brown oil. This material was flash chromatographed on silica gel with NH$_3$ saturated CHCl$_3$ as eluant to afford 0.62 g of the title compound above.

$^1$H NMR (CDCl$_3$): d 1.46 (s, 9H), 1.49 (s, 9H), 2.28 (s, 3H), 2.98 (m, 3H), 3.16 (m, 6H), 3.59 (m, 4H), 4.06 (br s, 2H), 6.76 (m, 2H), 6.93 (d, j=9 Hz, 2H), 7.43 (s, 1H), 7.65 (d, j=9 Hz, 2H), 7.80 (d, j=9 Hz, 2H)

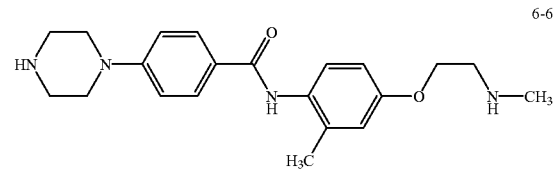

N-(2-Methyl-4-(2-methylaminoethoxy)phenyl)-4-(1-piperazinyl)benzamide (6-6)

To a 100 mL round bottomed flask with a stirring bar and a gas dispersion tube was added N-(2-methyl-4-(2-(1,1-dimethylethoxycarbonyl(methyl)amino)ethoxy)phenyl)-4-(4-(1,1-dimethylethoxycarbonyl)piperazin-1-yl)benzamide (0.620 g, 1.09 mmol) and 40 mL of dry EtOAc. This well stirred solution was cooled to 0° C. in an ice bath and was saturated with HCl gas for over 15 min. The reaction was aged for an hour and excess HCl was removed with a stream of argon. Removal of EtOAc in vacuo and the crude HCl salt was converting to freebase by dissolving in saturated NaHCO$_3$ solution. Extracted with EtOAc and the layers were separated. A white solid precipitated out from the aqueous and was collected via suction filtration. This crude product was recrystallized from hot MeOH-Et$_2$O to give 0.175 g of N-(2-methyl-4-(2-methylaminoethoxy)phenyl)-4-(1-piperazinyl)benzamide as a white solid. mp: 136–137° C. $^1$H NMR (DMSO-d$_6$): d 2.28 (s, 3H), 2.50 (s, 3H), 2.95 (m, 2H), 3.03 (m, 4H), 3.27 (m, 4H), 4.06 (m, 2H), 6.78 (d, j=6 Hz, 2H), 6.93 (d, j=9 Hz, 2H), 7.41 (s, 1H), 7.65 (d, j=9 Hz, 1H), 7.79 (d, j=9 Hz, 2H).

EXAMPLE 7

Tablet Preparation

Tablets containing 25.0, 50.0, and 100.0 mg., respectively, of the active compound N-(2-Methyl-4-(2-(N,N-dimethyl) aminoethoxy)-phenyl)-4-(1-piperazinyl)benzamide are prepared as illustrated below:

TABLE FOR DOSES CONTAINING
FROM 25-100 MG OF THE ACTIVE COMPOUND

|  | Amount-mg | | |
|---|---|---|---|
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 8

Intravenous formulations

An intravenous dosage form of the above-indicated active compound is prepared as follows:

| Active Compound | 0.5–10.0 mg |
|---|---|
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

What is claimed:

1. A compound having the formula

X—W—Y—Z—(A)$_r$—B or a pharmaceutically acceptable salt thereof, wherein
W is —(CH$_2$)$_q$—, wherein q is 0 or 2;
X is piperazinyl;
Y is

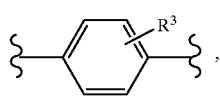

wherein R$^3$ selected from the group consisting of
hydrogen,
halogen,
C$_{1-10}$ alkyl,
C$_{3-8}$ cycloalkyl,
aryl,
aryl C$_{1-8}$ alkyl,
amino,
amino C$_{1-8}$ alkyl,
C$_{1-3}$ acylamino,
C$_{1-3}$ acylamino C$_{1-8}$ alkyl,
C$_{1-6}$ alkylamino,
C$_{1-6}$ alkylamino C$_{1-8}$ alkyl,
C$_{1-6}$ dialkylamino,
C$_{1-6}$ dialkylamino C$_{1-8}$ alkyl,
C$_{1-6}$ alkoxy,
C$_{1-6}$ alkoxy C$_{1-6}$ alkyl,
aryl C$_{1-6}$ alkyloxy,
aryl C$_{1-6}$ alkyloxy C$_{1-6}$ alkyl,
carboxy C$_{1-6}$ alkyl,
C$_{1-3}$ alkoxycarbonyl,
C$_{1-3}$ alkoxycarbonyl C$_{1-6}$ alkyl,
carboxy,
carboxy C$_{1-6}$ alkyloxy,
hydroxy, and
hydroxy C$_{1-6}$ alkyl;

Z is

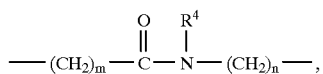

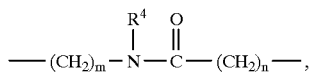

—CH$_2$CH$_2$—,

—CH=CH—,

—CH$_2$—O—,

—O—CH$_2$—,

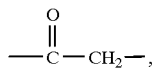

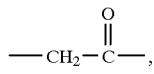

—CH$_2$NR$^4$—,

—NR$^4$CH$_2$—,

—SO$_2$—NR$^4$—,

—NR$^4$—SO$_2$—,

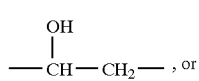

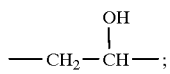

R$^4$ is selected from the group consisting of
hydrogen,
halogen,
C$_{1-10}$ alkyl,
C$_{3-8}$ cycloalkyl,
aryl,
aryl C$_{1-8}$ alkyl,
amino,
amino C$_{1-8}$ alkyl,
C$_{1-3}$ acylamino,
C$_{1-3}$ acylamino C$_{1-8}$ alkyl,
C$_{1-6}$ alkylamino,
C$_{1-6}$ alkylamino C$_{1-8}$ alkyl,
C$_{1-6}$ dialkylamino,
C$_{1-6}$ dialkylamino C$_{1-8}$ alkyl, C$_{1-4}$ alkoxy,
C$_{1-4}$ alkoxy C$_{1-6}$ alkyl,
carboxy,
carboxy$_{1-6}$ alkyl,
C$_{1-3}$ alkoxycarbonyl,
C$_{1-3}$ alkoxycarbonyl C$_{1-6}$ alkyl,
carboxy C$_{1-6}$ alkyloxy,
hydroxy, and
hydroxy C$_{1-6}$ alkyl;

A is

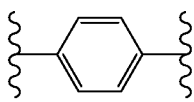

either unsubstituted or monosubstituted with R$^5$, or disubstituted with R$^5$ and R$^6$, or trisubstituted with R$^5$, R$^6$ and R$^{10}$, where R$^5$, R$^6$ and R$^{10}$ are independently selected from the group consisting of
hydrogen,
halogen,
C$_{1-10}$ alkyl,
C$_{3-8}$ cycloalkyl,
aryl,
aryl C$_{1-8}$ alkyl,
amino,
amino C$_{1-8}$ alkyl,
C$_{1-3}$ acylamino,
C$_{1-3}$ acylamino C$_{1-8}$ alkyl,
C$_{1-6}$ alkylamino,
C$_{1-6}$ alkylamino C$_{1-8}$ alkyl,
C$_{1-6}$ dialkylamino,
C$_{1-6}$ dialkylamino C$_{1-8}$ alkyl,
C$_{1-6}$ alkoxy,
C$_{1-6}$ alkoxy C$_{1-6}$ alkyl,
aryl C$_{1-6}$ alkyloxy,
aryl C$_{1-6}$ alkyloxy C$_{1-6}$ alkyl,
carboxy C$_{1-6}$ alkyl,
C$_{1-3}$ alkoxycarbonyl,
C$_{1-3}$ alkoxycarbonyl C$_{1-6}$ alkyl,
carboxy,
carboxy C$_{1-6}$ alkyloxy,
hydroxy, and
hydroxy C$_{1-6}$ alkyl;
r is 1;
B is —O(CH$_2$)$_p$CH$_2$N(R$^8$R$^7$),
—CH$_2$(CH$_2$)$_t$CH$_2$N(R$^8$R$^7$),
—CH(CH$_2$)$_t$CH$_2$N(R$^8$R$^7$), or
       |
       R$^9$

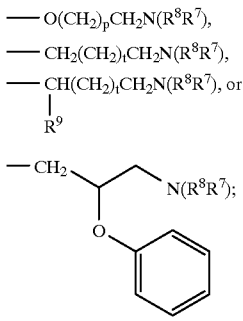

R$^7$, R$^8$, and R$^9$ are independently selected from the group consisting of
hydrogen,
halogen,
C$_{1-10}$ alkyl,
C$_{3-8}$ cycloalkyl,
aryl,
aryl C$_{1-8}$ alkyl,
amino,
amino C$_{1-8}$ alkyl,
C$_{1-3}$ acylamino,
C$_{1-3}$ acylamino C$_{1-8}$ alkyl,
C$_{1-6}$ alkylamino,
C$_{1-6}$ alkylamino C$_{1-8}$ alkyl,
C$_{1-6}$ dialkylamino,
C$_{1-6}$ dialkylamino C$_{1-8}$ alkyl,
C$_{1-6}$ alkoxy,
C$_{1-6}$ alkoxy C$_{1-6}$ alkyl,
aryl C$_{1-6}$ alkyloxy,
aryl C$_{1-6}$ alkyloxy C$_{1-6}$ alkyl,
carboxy,
carboxy C$_{1-6}$ alkyl,
C$_{1-3}$ alkoxycarbonyl,
C$_{1-3}$ alkoxycarbonyl C$_{1-6}$ alkyl,
carboxy,
carboxy C$_{1-6}$ alkyloxy,
hydroxy, and
hydroxy C$_{1-6}$ alkyl;
m is 0, 1, 2, 3, or 4;
n is an integer from 0 to 6;
p is 1, 2, 3 or 4;
s is an integer from 0 to 6; and
t is 0, 1, 2, 3 or 4.

2. A compound of claim 1 having the formula

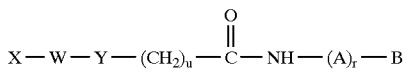

or a phamaceutically acceptable thereof, wherein
u is 0 or 1;
X is

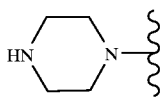

W is —(CH$_2$)$_q$—, wherein q is 0 or 2;
Y is

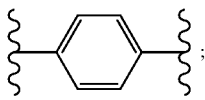

A is

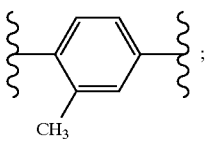

A is

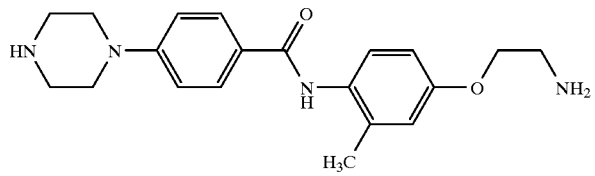

r is 1;
B is —O(CH$_2$)$_2$NH$_2$, —CH$_2$C(OPh)HCH$_2$NH$_2$, or —CH(CH$_3$)(CH$_2$)$_2$NH$_2$.

3. A compound of claim 2 which is

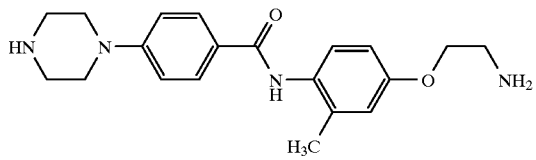

or a pharmaceutically acceptable salt thereof.

4. A composition comprising a therapeutically effective amount, compound of claim 1 and a pharmaceutically acceptable carrier.

5. A method for inhibiting the binding of fibrinogen to blood platelets in a mammal, comprising treating the mammal with a composition of claim 4.

6. A method for inhibiting the aggregation of blood platelets in a mammal, by blocking fibrinogen from acting at its receptor site, comprising treating the mammal with a composition of claim 4.

7. A composition for inhibiting the aggregation of blood platelets in a mammal, comprising an efficacious amount of a compound of claim 1 in combination with one or more agents selected from a thrombolytic agent, an anticoagulant agent, and an antiplatelet agent and a pharmaceutically acceptable carrier.

8. A method for inhibiting the aggregation of blood platelets in a mammal, by blocking fibrinogen from acting at its receptor site, comprising treating the mammal with a composition of claim 7.

9. A method for inhibiting the binding of fibrinogen to blood platelets in a mammal, by blocking fibrinogen from acting at its receptor site, comprising treating the mammal with a composition of claim 7.

10. A method for inhibiting osteoclast mediated bone resorption, comprising treating the mammal with a composition of claim 4.

11. A method for inhibiting angiogenesis in a mammal comprising treating the mammal with a composition of claim 4.

12. A method for inhibiting tumor growth in a mammal comprising treating the mammal with a composition of claim 4.

* * * * *